(12) United States Patent
Funke et al.

(10) Patent No.: US 6,576,796 B1
(45) Date of Patent: Jun. 10, 2003

(54) PROCESS FOR THE PREPARATION OF ALKYLAMINES

(75) Inventors: Frank Funke, Frankenthal (DE); Ulrich Steinbrenner, Neustadt (DE); Matthias Frauenkron, Ludwigshafen (DE); Ralf Böhling, Griesheim (DE); Johann-Peter Melder, Böhl-Iggelheim (DE); Thomas Heidemann, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/668,458

(22) Filed: Sep. 25, 2000

(30) Foreign Application Priority Data

| Jun. 28, 2000 | (DE) | ......................... 100 30 619 |
| Aug. 24, 2000 | (DE) | ......................... 100 41 676 |

(51) Int. Cl.[7] ............................................. C07C 209/60
(52) U.S. Cl. ....................................... 564/470; 564/485
(58) Field of Search .................................. 564/470, 485

(56) References Cited

U.S. PATENT DOCUMENTS

| 2,501,556 A | 3/1950 | Whitman ..................... 260/563 |
| 2,750,417 A | 6/1956 | Closson et al. .............. 260/577 |
| 3,758,586 A | 9/1973 | Coulson ....................... 260/583 |

(List continued on next page.)

FOREIGN PATENT DOCUMENTS

| DE | 510 439 | 10/1930 |
| DE | 697372 | 10/1940 |
| DE | 2 117 970 | 10/1971 |
| DE | 36 34 247 | 7/1987 |
| DE | 195 24 242 | 1/1997 |
| DE | 196 24 206 | 1/1998 |
| EP | 0 039 918 | 11/1981 |
| EP | 0 054 746 | 6/1982 |
| EP | 132 736 | 2/1985 |
| EP | 200 923 | 11/1986 |
| EP | 752 409 | 1/1997 |
| EP | 822 179 | 2/1998 |
| FR | 1484782 | 9/1967 |
| GB | 1294 418 | 10/1972 |
| WO | 96/07630 | 3/1996 |

OTHER PUBLICATIONS

Weissermel et al. "Industrielle Organische Chemie" (1994) pp. 70–76.
Möller "Erasatz von Aminogruppen durch andere Aminogruppen" Shichslottrerbiudunger II vol. XI (1957) pp. 248–261.
Lehmkulh et al. "Katalytishce eaktionen von Aminen Mit Olefinen" J. Organometallic Chemistry vol. 55 (1973) pp. 215–220.
Steinborn et al. "Zur Komplexkatalyse der Aminomethylierung und Aminierung von Olefinen" Zietschrift für Chemie vol. 26 (1986) pp. 349–359.
Closson et al. "Base–Catalyzed Alkylation with Olefins" J. Am. Chem. Soc. vol. 22 (1936) pp. 646–649.
Pez et al. "Metal amide catalyzed lamination of olefins" Pure & Appl. Chem vol. 57, No. 12 (1985) pp. 1917–1926.
Brunet "Hydroamination of Alkenes, Amidorhodium Catalyst" Gazetta Chimica Italiana vol. 127 (1997) pp. 111–118.
Deeba et al. "Direct lamination of olefins: A comparative study over erionite and Y zeolites" Zeolites vol. 10 (1990) pp. 794–797.

(List continued on next page.)

Primary Examiner—Brian J. Davis
(74) Attorney, Agent, or Firm—Keil & Weinkauf

(57) ABSTRACT

Preparation of alkylamines, where, in a first process stage, an olefin is reacted with ammonia, a primary amine and/or a secondary amine under hydroaminating conditions, and then, in a second process stage, the resulting hydroamination product(s) is/are reacted under transalkylating conditions.

16 Claims, 3 Drawing Sheets

U.S. PATENT DOCUMENTS

| | | | |
|---|---|---|---|
| 4,204,997 A | 5/1980 | Hobbs et al. | 260/326 |
| 4,302,603 A | 11/1981 | Pez | 564/485 |
| 4,336,162 A | 6/1982 | Pez | 252/438 |
| 4,454,321 A | 6/1984 | Gardner et al. | 546/184 |
| 4,582,904 A | 4/1986 | Wells et al. | 544/178 |
| 4,929,758 A | 5/1990 | TaglieBer et al. | 564/485 |
| 5,763,668 A | 6/1998 | Dingerdissen et al. | 564/485 |
| 5,780,681 A | 7/1998 | Eller et al. | 564/485 |
| 5,892,125 A | 4/1999 | Kanand et al. | 568/449 |

OTHER PUBLICATIONS

Beller et al. "Basenkatalysierte Synthese von N–(2–Arylethyl)anilenen und basenvermittelte Dominosynthese von 2,3–Dihydroinodolen" Angew. Chem. vol. 110 (1998) pp. 3571–3573.

Kakuno et al. "Addition of amines to conjugated dienes catalyzed by solid base catalyst" Jour. of Catalyst vol. 85 (1984) pp. 509–518.

Haak et al. "Katalytische Hydroaminierung von Alkenen und Alkinen" Organische Chemie vol. 5, (1999) pp. 297–303.

Müller et al. "Metal Initiated Amination of Alkenes and Alkynes" Chem. Rev. vol. 98 (1998) pp. 675–697.

Steinborn et al. "Under die Metallamidkatalysierte Umsetzung von Sekundären Aminen mit Ethen" Z. Chem vol. 29 (1989) pp. 333–334.

Stroh et al. "Neuere Methoden der präparativen organischen Chemie" Angew Chem. vol. 69 (1957) pp. 124–131.

Howk et al. "Alkali–Metal Catalyzed Amination of Olefins" J. Am. Chem Soc. vol. 76 (1954) pp. 1899–1902.

Ullmann's Encyclopedia of Industrial Chemisty vol. A2 p. 4.

*Ullmann's Enc. of Ind. Chem.*, 6th Ed., 2000, (Electronic Release) "General Production Methods for Aliphatic Amines.".

PROCESS FOR THE PREPARATION OF ALKYLAMINES

The present invention relates to a process for the preparation of alkylamines.

Alkylamines are starting materials for the preparation of surfactants, textile and flotation auxiliaries, bactericides, corrosion and foam inhibitors, additives for pharmaceuticals, and as antioxidants for fats and oils.

Alkylamines can be prepared by the hydrogenation of corresponding nitriles or nitro compounds, by the reductive amination of corresponding aldehydes and ketones and by the amination of corresponding alcohols.

The lower alkylamines ($C_1$- to $C_{10}$-alkylamines), such as the ethylamines, butylamines and isopropylamines, are prepared industrially in particular by the amination of the corresponding alcohol or of the corresponding carbonyl compound over metal catalysts, which are e.g. supported, under hydrogenating conditions (see e.g.: Ullmann's Encyclopedia of Industrial Chemistry, Vol. A 2, $5^{th}$ Ed., page 4).

Alternatively, alkylamines can also be prepared over acidic phoshate catalysts from corresponding alcohols (see e.g. U.S. Pat. No. 4,582,904 (Air Products)).

A further alternative for the preparation of alkylamines consists in the addition of $NH_3$ or amines to olefins in the presence of acidic catalysts, such as zeolites (see e.g. EP-A-132 736), in the presence of basic catalysts, such as metal amides, in particular alkali metal amides and alkaline earth metal amides, (see e.g. B. W. Howk et al., J. Am. Chem. Soc. 76, page 1899ff (1954); R. Stroh et al., Angew. Chem. 69, 124ff (1957)), amides of subgroup IV (see e.g. D. Steinborn et al. (Z. Chem. 29 (1989), page 333ff) or alkali metal alkoxides, or in the presence of transition metal complex compounds (see e.g. U.S. Pat. No. 3,758,586).

However, to date this alternative has scarcely been used industrially.

The processes listed above for the preparation of alkylamines have the following disadvantages:

The use of alcohols (e.g. ethanol), aldehydes, ketones and nitriles as starting materials for the preparation of alkylamines is significantly less economical based on their prices than the use of corresponding olefins (e.g. ethene).

The use of olefins as starting material for the preparation of alkylamines is accordingly desirable, but has hitherto been burdened with the following disadvantages (cf. e.g.: M. Beller et al., Chem. Rev. 98, 675f (1998) 675; R. Taube, 'Reaction with Nitrogen Compounds' in B. Cornils and W. A. Hermann: 'Applied Homogeneous Catalysis with Organometallic Compounds', VCH Weinheim, 1996, pages 507 to 520, and E. Haak et al., Chemie in unserer Zeit (1999), 297 to 303, in particular the summary on p. 302):

aa) The addition, under basic and heterogeneous catalysis, of amines to olefins over metal oxides is possible, according to Kakuno et al. (J. Catal. 85 (1984), page 509ff), with primary and secondary alkylamines and conjugated dienes, such as butadiene or isoprene; the general use of $NH_3$ or monoolefins is not described.

ab) The addition, under weakly basic catalysis, of amines to olefins using alkali metal alkoxide as catalyst is, according to Beller et al. (Angew. Chem. 110 (1998), page 3571ff), successful in the case of aromatically conjugated amines and styrene as olefin component. In the case of $NH_3$ or monoolefin as starting material, the catalysts are inactive.

ac) In the case of the $NaNH_2$- or $KNH_2$-catalyzed addition of $NH_3$ to olefins, as is described e.g. in B. W. Howk et al., J. Am. Chem. Soc. 76 (1954), 1899–1902 and R. D. Closson et al., U.S. Pat. No. 2,750,417, the space-time yields of desired alkylamines are very low even at high temperatures and olefin pressures because of the low activity and solubility of the metal amide.

ad) G. P. Pez (U.S. Pat. Nos. 4,336,162 and 4,302,603) describes a solution to this problem by changing to the Rb and Cs amides or using a eutectic of $NaNH_2$ and $KNH_2$. In the first case, industrial realization is precluded due to the extremely high price of the catalyst, and in the second case the space-time yields of desired alkylamines are still too low.

ae) Alkali metal monoalkylamides or alkali metal dialkylamides can be used as strong bases for the addition of olefins, such as ethylene, to amines with sufficient space-time yields, although in the presence of $NH_3$ immediate protolysis of the corresponding alkali metal alkylamide to give $MNH_2$ (M=alkali metal) occurs. This again has the disadvantages already listed above.

However, the alkali metal alkylamide-catalyzed addition of amines to olefins in the absence of $NH_3$ again has the disadvantage that relatively expensive amines have to be used as starting materials instead of low-cost ammonia.

b) Over acidic catalysts, such as zeolites, the addition of $NH_3$ to olefins, ammonia generally being used in a high excess based on the olefin, does not proceed in every case with such good selectivities and yields for a certain alkylamine as, for example, in the case of isobutene (see e.g. DE-A-36 34 247).

Thus, for example, M. Deeba et al. in Zeolites 10 (1990), page 794ff, and in Chem. Ind. 40 (1990), page 241ff, in the case of the reaction of ethylene and $NH_3$ over zeolites, and Gardner et al. in EP-A-200 923 in the case of the reaction of ethylene and $NH_3$ in the presence of $NH_4I$, found predominantly monoethylamine, in addition to small amounts of diethylamine and very small amounts of triethylamine.

One solution would be the hydroamination of olefins with $NH_3$ in substoichiometric amount, although in this case poor selectivities based on the olefin are generally achieved and rapid deactivation of the catalyst results.

The hydroamination of olefins with secondary amines in the presence of acidic catalysts again generally proceeds in poorer yields and with poorer selectivities than the corresponding hydroamination with ammonia or primary amines.

c) The transition metal complex-catalyzed hydroamination of olefins is generally possible in good yields only with secondary alkylamines (e.g.: Brunet, Gazzetta Chimica Italiana, 127, 1997, pages 111 to 118, page 112, left-hand column).

It is an object of the present invention to find, while overcoming the disadvantages of the prior art, an alternative, economical and flexible process for the preparation of alkylamines which permits the preparation of a desired alkylamine or two or more desired alkylamines with a high space-time yield and selectivity.

We have found that this object is achieved by a process for the preparation of alkylamines which comprises, in a first process stage, reacting an olefin with ammonia, a primary amine and/or a secondary amine under hydroaminating conditions, and then, in a second process stage, reacting the resulting hydroamination product(s) under transalkylating conditions.

In a preferred embodiment of the process, in the balance of the feed materials olefin and ammonia, primary amine and/or secondary amine, only ammonia and olefin are consumed by establishing corresponding recycle streams of amines resulting from the first and/or second process stage to the feed of the first and/or second process stage.

Olefins or mixtures thereof which can be used in the process according to the invention are generally olefins of the formula

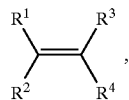    I in which

R¹, R², R³, R⁴ are hydrogen (H), $C_1$- to $C_{20}$-alkyl, $C_2$- to $C_{20}$-alkenyl, $C_3$- to $C_{20}$-cycloalkyl, $C_5$- to $C_8$-cycloalkenyl, $C_6$- to $C_{20}$-alkylcycloalkyl, $C_6$- to $C_{20}$-cycloalkylalkyl, aryl, $C_7$- to $C_{20}$-alkylaryl and $C_7$- to $C_{20}$-aralkyl, and R¹ and R³ can additionally together be a $C_2$- to $C_{12}$-alkylene chain.

Examples of such olefins are ethene, propene, 1-butene, 2-butene, isobutene, 1-pentene, 2-pentene, 1-hexene, 2-hexene, 3-hexene, 1-octene, isooctene, 1-decene, styrene, stilbene, cyclopentene, cyclohexene, allene, 1,3-butadiene, isoprene and 4-vinyl-1-cyclohexene.

Primary and secondary amines or mixtures thereof which can be used in the process according to the invention are generally amines of the formula

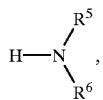    II in which

R⁵ is hydrogen (H), $C_1$- to $C_{20}$-alkyl, $C_2$- to $C_{20}$-alkenyl, $C_3$- to $C_{20}$-cycloalkyl, alkoxyalkyl, aminoalkyl, monoalkylaminoalkyl, dialkylaminoalkyl, aralkyl and R⁶ is $C_1$- to $C_{20}$-alkyl, $C_2$- to $C_{20}$-alkenyl, $C_3$- to $C_{20}$-cycloalkyl, alkoxyalkyl, aminoalkyl, monoalkylaminoalkyl, dialkylaminoalkyl, aralkyl, and R⁵ and R⁶ can together be a saturated or unsaturated $C_3$- to $C_9$-alkylene chain, which may be interrupted by an O, S or N heteroatom, in particular are together a —(CH₂)ⱼ—X—(CH₂)ₖ— group, where j and k=1 to 4 and X=CH₂, CHR⁷, oxygen (O), sulfur (S) or NR⁷, where R⁷=H or $C_1$- to $C_4$-alkyl.

Examples of such primary amines are methylamine, ethylamine, n-propylamine, isopropylamine, n-butylamine, isobutylamine, tert-butylamine, n-pentylamine, cyclopentylamine, isopentylamine, n-hexylamine, cyclohexylamine, n-octylamine, n-decylamine, 1-phenylethylamine, 2-phenylethylamine, allylamine, 2-dimethylaminoethylamine and 2-methoxyethylamine.

Examples of secondary amines according to formula II are dimethylamine, diethylamine, di-n-propylamine, diisopropylamine, di-n-butylamine, pyrrolidine, piperidine, hexamethylenamine, piperazine and morpholine.

The alkylamines or mixtures thereof prepared by the process according to the invention are generally alkylamines of the formulae

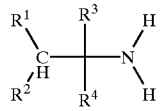    VI

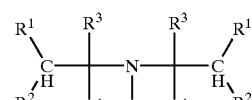    VII

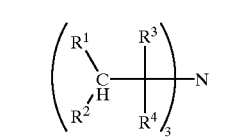    VIII

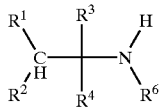    IV

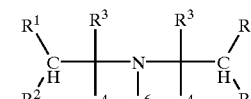    V

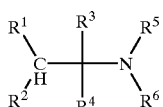    III where R¹ to R⁶ have the meanings given above.

To improve the clarity of the above scheme, regioisomers of V, VII and VIII (analogous to the regioisomers Va and Vb given in the reaction schemes below) are not shown, but are also included.

If the transalkylation in the second process stage is carried out over a hydrogenation- or dehydrogenation-active catalyst in the presence of H₂, any unsaturated radicals R¹ to R⁶ are converted into the corresponding saturated radicals, possibly in the same process step.

Examples of such alkylamines prepared in accordance with the process are monoethylamine, diethylamine, triethylamine, n-propylamine, di-n-propylamine, tri-n-propylamine, isopropylamine, diisopropylamine, n-butylamine, di-n-butylamine, tri-n-butylamine, isobutylamine, tert-butylamine, n-pentylamine, isopentylamine, cyclopentylamine, n-hexylamine, cyclohexylamine, n-octylamine, n-decylamine, 2-phenylethylamine, N-ethylpyrrolidine, N-ethylpiperidine, N-ethylhexamethylenamine, N-ethylpiperazine and N-ethylmorpholine.

The process can be carried out as follows:

First Process Stage

In the first process stage an olefin, in particular an olefin of the formula I, is reacted with ammonia, a primary amine and/or a secondary amine, in particular ammonia, a primary amine and/or secondary amine of the formula II, under hydroaminating conditions.

Advantageously, the feed for the first process stage can also have passed/returned to it ammonia and/or amines from the reaction discharge of this first process stage and/or from the second process stage.

a)

In particular, in the first process stage, an olefin, in particular an olefin of the formula I, is reacted with a primary amine and/or a secondary amine, in particular a primary amine and/or secondary amine of the formula II, very particularly a secondary amine of the formula II, in the presence of a metal monoalkylamide or metal dialkylamide or mixtures thereof as catalyst under hydroaminating conditions.

The reaction generally takes place according to the following reaction scheme.

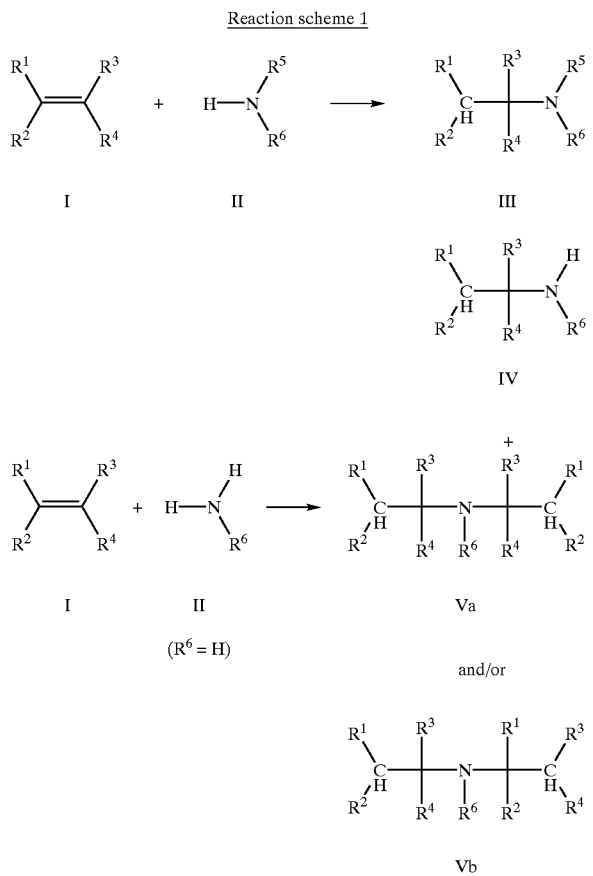

Reaction scheme 1

To simplify the above scheme it is assumed that where the radicals $R^1$ to $R^4$ in I are saturated, the resulting olefininc double bond is neither in the α- nor in the β-position relative to the nitrogen in III, IV or V. However, in reality, under the basic conditions in the first process stage it is entirely possible for double-bond isomerization to arise.

Very particularly preferred olefins I are ethene ($R^1$, $R^2$, $R^3$ and $R^4$=H), 1,3-butadiene ($R^1$, $R^3$ and $R^4$=H and $R^2$=CH=CH$_2$) and propene ($R^1$, $R^2$, $R^3$=H and $R^4$=CH$_3$).

Very particularly preferred amines are mono- and dialkylamines, such as monoethylamine, diethylamine, n-butylamine, di-n-butylamine and isopropylamine.

Hydroamination products starting from ethene and monoethylamine are di- and/or triethylamine, starting from ethene and diethylamine: triethylamine, starting from isopropylamine and propene: diisopropylamine, starting from 1,3-butadiene and n-butylamine: butenyl-n-butylamines and starting from isoprene and isopentylamine: isopentylmethylbutenylamines.

Metal dialkylamides are preferred over metal monoalkylamides as catalysts.

The metal monoalkylamides and metal dialkylamides generally have the formula MNR$^7$R$^8$ (M=monovalent metal), M(NR$^7$R$^8$)$_2$ (M=divalent metal), M(NR$^7$R$^8$)$_3$ (M=trivalent metal) or M(NR$^7$R$^8$)$_4$ (M=tetravalent metal), where $R^7$ has the meanings according to the radical $R^5$, and $R^8$ has the meanings according to the radical $R^6$, and $R^7$ and $R^8$ can also together be a saturated or unsaturated C$_3$- to C$_9$-alkylene chain, which may be interrupted by an O, S or N heteroatom (as defined for $R^5$ and $R^6$), in particular can together be a —(CH$_2$)$_j$—X—(CH$_2$)$_k$— group (as defined for $R^5$ and $R^6$) (see above).

Particularly preferably, the metal monoalkylamides and metal dialkylamides have the formula MNR$^5$R$^6$, M(NR$^5$R$^6$)$_2$, M(NR$^5$R$^6$)$_3$ or M(NR$^5$R$^6$)$_4$, in which, accordingly, the radicals R correspond to those of the primary and/or secondary amine used.

Preferred metal components (M) in the metal monoalkylamide and metal dialkylamide catalysts are metals of Groups IA, IIA, IIIB and IVB (Li, Na, K, Rb, Cs, Mg, Ca, Sr, Ba, Sc, Y, La or a lanthanide element, Ti, Zr or Hf), in particular Li, Na, Mg, Ca and K, very particularly Na and K.

Examples of such metal alkylamides are NaHNEt, NaNEt$_2$, KHNEt, KNEt$_2$, LiHNEt, LiNEt$_2$, LiN(isoC$_3$H$_7$)$_2$, NaN(isoC$_3$H$_7$)$_2$, NaN(n-C$_4$H$_9$)$_2$, NaHN(isoC$_3$H$_7$), NaHN (isopentyl), Mg(NEt$_2$)$_2$, Ca(NPr$_2$)$_2$ and Zr(NEt$_2$)$_4$.

In the case of the hydroamination of ethene with monoethylamine and/or diethylamine, NaNEt$_2$ and KNEt$_2$ are particularly preferred.

In the case of the hydroamination of di-n-butylamine with butadiene, NaN(nBu)$_2$ and KN(nBu)$_2$ are particularly preferred, and in the case of that of n-butylamine with butadiene, NaHNnBu and KHNnBu are particularly preferred.

These metal monoalkylamides and metal dialkylamides are prepared as described in Houben-Weyl, Methoden der organischen Chemie [Methods in Organic Chemistry], 4$^{th}$ edition, Volume XI/2 (Nitrogen Compounds II and III), Verlag Thieme, Stuttgart, p. 182ff, in U.S. Pat. No. 4,595,779, WO 93/14061, DE-A-21 17 970, DRP 615,468, GB-A-742 790, DE-A-26 13 113, U.S. Pat. No. 2,750,417, J. Wollensak, Org. Synth. 43 (1963), page 45ff, or C. A. Brown, J. Am. Chem. Soc. 95(3) (1973), page 982ff, by reacting metal with the corresponding amine in the presence of an unsaturated compound, such as butadiene, isoprene, naphthalene, pyridine or styrene, by reacting a metal amide or hydride with the corresponding amine, or by reacting an organometallic compound, such as n-BuLi, MeLi, PhNa, Et$_2$Mg or Et$_4$Zr, with the corresponding amine.

The reaction of the olefin with the amine in the presence of the metal alkylamide (first process stage) can, for example, be carried out as described in G. P. Pez et al., Pure & Appl. Chem. 57(12), 1917–26 (1985), R. D. Closson et al., J. Org. Chem. 22 (1957), 646–9, G. M. Whitman et al., U.S. Pat. No. 2,501,556), D. Steinborn et al., Z. Chem. 29 (1989), 333–4, D. Steinborn et al., Z. Chem. 26 (1986) 349–59 and H. Lehmkuhl et al., J. Organomet. Chem. 55 (1973), 215–20.

The reaction of the olefin with the amine in the presence of the metal alkylamide can also be carried out in the presence of small amounts of ammonia (less than 1 mol % based on the amine(s) used) (cf. DE-A-21 17 970).

The preparation of the metal alkylamide and the catalytic hydroamination of the olefin can also be carried out in a "one-pot synthesis", i.e. simultaneously.

For this, e.g. BuLi, C$_2$H$_4$ and diethylamine or Na, diethylamine, C$_2$H$_4$ and a small amount of butadiene are used as reaction mixture.

If the olefin to be hydroaminated has conjugated double bonds, such as butadiene, isoprene and also styrene, the synthesis is then preferably carried out as "one-pot synthesis".

The metal alkylamide can be converted into metal hydride during the reaction by β-elimination or action of $H_2$ as described in DE-A-26 13 113; in the case of the β-elimination an imine forms in parallel during the process. This can be converted back into metal alkylamide and $H_2$ by the action of a primary or secondary amine as in DE-A-26 13 113, C. A. Brown, J. Am. Chem. Soc. 95(3) (1973), 982ff or C. A. Brown, Synthesis (1978), 754ff, meaning that the metal hydride can be regarded as a type of "rest form" of the metal alkylamide and therefore for the purposes of the present invention is to be equated with the metal alkylamide.

Furthermore, complexing agents may be present as solvent both during the preparation of the catalyst and also during the reaction.

Thus, e.g. J. F. Remenar (J. Am. Chem. Soc. 120 (1988), 4081ff), H. Lehmkuhl et al. (J. Organomet. Chem. 55 (1973), 215ff) and D. Steinborn et al. (Z. Chem. 29 (1989), 333ff) describe the use of N,N,N',N'-tetramethylethylenediamine, N,N,N',N'',N''-pentamethyldiethylenetriamine, N,N,N',N'-tetramethylcyclohexanediamine and tetrahydrofuran as complexing agents.

Moreover, amines having two or more aminic N atoms per molecule, such as N,N,N',N'-tetraethylethylenediamine, N-permethylated or N-perethylated triethylenetetramine up to N-permethylated or N-perethylated polyimine having molecular masses up to 500,000 Dalton, ethers and polyethers, such as diglymes, triglymes and the corresponding homologs, terminally capped polyols—e.g. PEG, PPG, poly-THF—, and complexing agents having aminic N and etheric O atoms in the molecule, such as 3-methoxyethylamine, 3-(2-methoxyethoxy)propylamine or N,N,N',N'-tetramethyldiaminodiethyl ether, may be present.

The normal procedure involves dissolving or suspending the catalyst (or the corresponding metal hydride or the corresponding organometallic compound (e.g. n-BuLi) as catalyst 'precursor') in a primary and/or secondary amine, particularly preferably in a secondary amine. The solvent used is preferably the amine mixture which automatically arises from the feed of the first process stage and the products of the hydroamination.

The catalyst can be in the form of a solution, suspension or supported on a typical catalyst support, such as $SiO_2$, $Al_2O_3$, $TiO_2$, $ZrO_2$, active carbon, MgO, $MgAl_2O_4$. The catalyst is preferably in the form of a solution or suspension, particularly preferably in the form of a solution.

The hydroamination of the olefin can be carried out discontinuously, semicontinuously or continuously.

In the first case, the olefin is added to catalyst and amine and reacted. In the second case, the olefin is metered into the reaction mixture. In the third case, catalyst, amine and olefin are metered in continuously.

Preference is given to an olefin: secondary amine molar ratio of 3:1 to 1:10, particularly preferably 1:1 to 1:2.

Preference is given to an olefin:primary amine ratio of from 6:1 to 1:5, particularly preferably 2:1 to 1:1.

The reaction is preferably carried out with stirring at 0 to 250° C., in particular at 20 to 150° C. and particularly preferably at 40 to 120° C.

The reaction can be carried out under the pressure which results under the chosen conditions (autogenous pressure). The pressure while the reaction is being carried out is generally 0 to 200 bar gage, in particular 2 to 100 bar gage, very particularly 3 to 30 bar gage.

Suitable reactors are all typical reaction apparatuses, e.g. stirred reactors, loop reactors, bubble columns, packed bubble columns, cascaded bubble columns and stirred columns.

After the reaction, the product is separated from the catalyst, e.g. by distillation, rectification, filtration, membrane filtration, washing with water or adsorption.

Catalyst (metal alkylamide or metal hydride) which has not undergone protolysis can then be recycled.

b)

Alternatively, in particular, in the first process stage, an olefin, in particular an olefin of the formula I, is reacted with ammonia and/or a primary amine, in particular ammonia and/or a primary amine of the formula II, in the presence of an inorganic solid-state acid as catalyst or mixtures thereof under hydroaminating conditions.

The reaction is generally carried out according to the reaction scheme below.

Reaction scheme 2

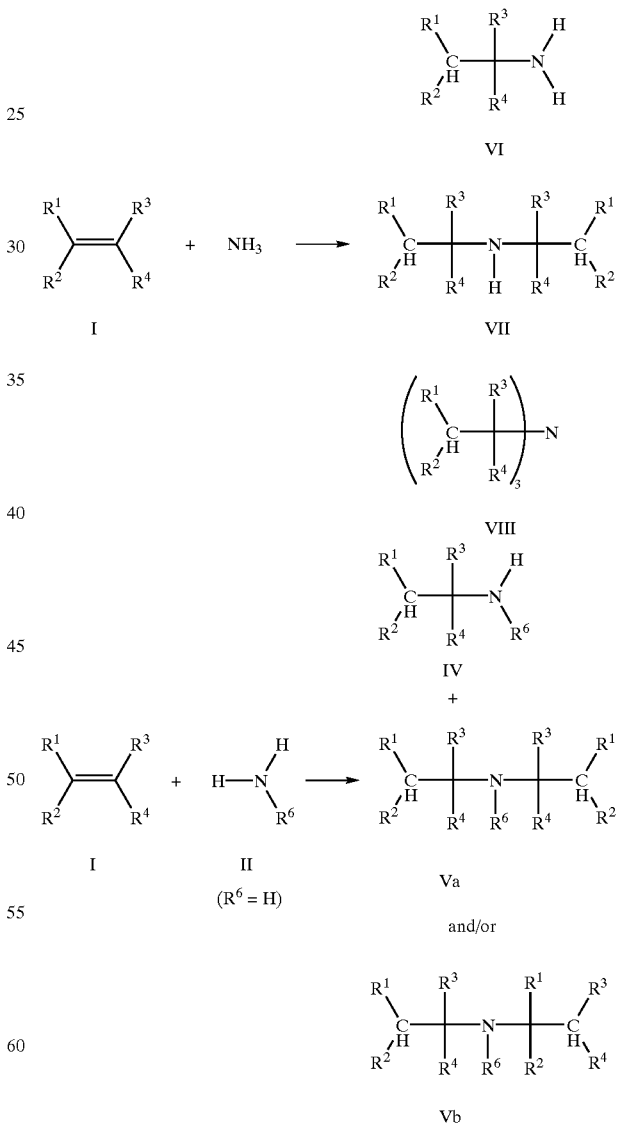

For simplicity, it is assumed here that where the radicals $R^1$ to $R^4$ in I are unsaturated, the resulting olefinic double bond is neither in the α- nor in the β-position relative to the nitrogen in IV, V, VI, VII or VIII. However, in reality, under the acidic conditions of the first process stage, it is entirely possible for double-bond isomerization to arise.

To improve the clarity of the above scheme, regioisomers of VII and VIII, analogously to the regioisomers Va and Vb, are not shown, but are also included.

Very particularly preferred olefins I are ethene ($R^1$, $R^2$, $R^3$ and $R^4$=H), propene ($R^1$, $R^2$ and $R^4$=H and $R^3$=$CH_3$), 1- and 2-butene ($R^1$, $R^2$ and $R^4$=H and $R^3$=$C_2H_5$ or $R^1$ and $R^3$ H and $R^2$ and $R^4$=$CH_3$), 1,3-butadiene ($R^1$, $R^3$ and $R^4$=H and $R^2CH$=$CH_2$) and isobutene ($R^3$ and $R^4$=$CH_3$, $R^1$ and $R^2$=H) .

Particularly preferred amines are $NH_3$ and monoalkylamines, particular preference being given to $NH_3$, monoethylamine, n-butylamine and isopropylamine, and very particular preference being given to $NH_3$.

Hydroamination products starting from ethene and ammonia are mainly monoethylamine, a small amount of diethylamine and a very small amount of triethylamine, starting from ethene and monoethylamine: mainly diethylamine and a small amount of triethylamine, starting from isobutene and ammonia: tert-butylamine, starting from 1,3-butadiene and ammonia: 1-amino-2-butene and/or 2-amino-3-butene, starting from propene and ammonia: isopropylamine and starting from butenes and ammonia: 2-butylamine.

The inorganic solid-state acid used as catalyst is defined by the fact that it (1.) has more than 50 $\mu$mol/g of acid centers at a pKa value of less than 3.3 and (2.) is thermally stable up to at least 400° C.

The number of acid centers is determined here according to the Hammett titration method using dimethyl yellow [CAS No. 60-11-7] as indicator and n-butylamine as probe in accordance with H. A. Benesi and B. H. C. Winquist in Adv. Catal., Vol. 27, Academic Press 1978, p. 100ff.

Examples of such inorganic solid-state acids are zeolites and alumosilicates, aluminum phosphates and silica alumophosphates, mixed acidic metal oxides and acidic metal oxides having a high surface area, phyllosilicates, and supported and unsupported ammonium halides.

Suitable catalysts for the hydroamination of olefins with ammonia and/or a primary amine are zeolites, in particular faujasites such as X, Y and USY zeolite, erionite, chabazite, mordenite, offretite, clinoptiolite, pentasils such as ZSM-5 and ZBM-10, ZSM-11, ZSM-12, MCM-22, MCM-41, MCM-48, MCM-49, MCM-56, EMT, SSZ-26, SSZ-33, SSZ-37, CIT-1, PSH-3, NU-85, beta and the boron-containing forms, such as ZBM-11, H-boron-ZSM-5, H-boron-beta, H-boron-ZSM-11, and the gallium- or titanium-containing forms. They are notable for a high number of catalytically active centers, combined with a large surface area.

The zeolites described differ in type and in the nature of the aftertreatment following their preparation (e.g. thermal treatment, dealuminization, acid treatment, metal ion exchange etc.).

Examples of suitable zeolites are given in U.S. Pat. Nos. 4,375,002, 4,536,602, EP-A-305 564, EP-A-101 921 and DE-A-42 06 992.

The zeolites known from EP-A-133 938, EP-A-431 451 and EP-A-132 736, which are boron, gallium, alumino- and iron silicate zeolites, which may optionally be doped as described with alkali metals, alkaline earth metals and transition metals, are also suitable.

Furthermore, the beta zeolites known from CA-A-2 092 964, which are defined as crystalline aluminosilicates of a specific composition having a pore size of more than 5 Å, are, for example, also suitable.

Preference is given to using metal- or halogen-modified beta zeolites, as described, for example, in DE-A-195 30 177.

Zeolite catalysts of the pentasil type having an $SiO_2$/$Al_2O_3$ molar ratio of greater than/equal to 10, as disclosed in EP-A-132 736, are particularly suitable.

The aluminum phosphates and silicoalumophosphates include the crystalline systems having zeolite structures or zeolite-like structures, such as SAPO-37, $AlPO_4$-5, SAPO-5, as described in DE-A-196 01 409, and also amorphous systems as described, for example, in DE-A-44 31 093. They generally have the formula $Al_2O_3 * P_2O_5 * xSiO_2$.

Suitable mixed metal oxides are also the systems which Tanabe et al. describes in Bull. Chem. Soc. Jpn. 47 (1974), p. 1064ff, in particular $Al_2O_3$—$TiO_2$, $SiO_2$—$TiO_2$, $ZrO_2$—$TiO_2$, $Fe_2O_3$—$TiO_2$, $WO_3$—$TiO_2$, $MoO_3$—$TiO_2$, $Nb_2O_5$—$TiO_2$, $Al_2O_3$—$B_2O_3$, $SiO_2$—$Ga_2O_3$, $SiO_2$—$B_2O_3$, $SiO_2$—$Y_2O_3$, $SiO_2$—$ZrO_2$, $SiO_2$—$WO_3$, $SiO_2$—$MoO_3$, $ZrO_2$—$MoO_3$, $ZrO_2$—$WO_3$.

Examples of the amination of olefins using these oxides are given in DE-A-196 24 206.

The phyllosilicates which can be used as catalyst are, in particular, clays of the montmorillonite-saponite group, the kaolin-serpentine group and polygorsite-sepiolite group, e.g. montmorillonite, hectorite, kaolin, sauconite, as described in Klockmanns Lehrbuch der Mineralogie (Klockmann's Handbook of Mineralogy), 16th ed., F. Euke Verlag (1978), pages 739–765. In addition, these phyllosilictes can also be modified, e.g. by so-called "pillaring" (the PILC's) or by acid activation (e.g. Tonsil, K10 and K20 from Südchemie AG, Munich).

Examples of the preparation of amines from olefins and $NH_3$ using phyllosilicates are given in DE-A-195 24 242.

Furthermore, these acid catalysts may also contain material which is already spent, or consist of material which has been regenerated by the customary methods, e.g. by recalcination in air, $H_2O$, $CO_2$ or inert gas at temperatures greater than 200° C., by washing with $H_2O$, acids or organic solvents, by steaming or by treatment under reduced pressure at temperatures greater than 200° C.

They can-be used in the form of powders or, preferably, in the form of moldings, such as strands, tablets or chips. For the shaping, 2 to 60% by weight (based on the mass to be shaped) of binder can be added. Suitable binders are various aluminum oxides, preferably boehmite, amorphous aluminosilicates having a molar $SiO_2$/$Al_2O_3$ ratio of from 25:75 to 95:5, silicon dioxide, preferably highly disperse $SiO_2$, such as silica sols, mixtures of highly disperse $SiO_2$ and highly disperse $Al_2O_3$, highly disperse $TiO_2$, and clays.

Following shaping, the extrudates or compacts are advantageously dried at 110° C./16 h and calcined at 300 to 500° C./2 to 16 h, it also being possible for the calcination to be carried out directly in the hydroamination reactor.

The catalysts are usually used in the H form. However, to increase the selectivity, the service life and the number of possible catalyst regenerations, it is additionally possible to carry out various modifications on the catalysts.

A modification of the catalysts consists in the possible ion exchange or doping of unshaped catalysts with alkali metals, such as Na and K, alkaline earth metals, such as Ca, Mg, earth metals such as Tl, transition metals, such as Mn, Fe, Mo, Cu, Zn, Cr, noble metals and/or rare earth metals, such as La, Ce or Y.

An advantageous catalyst variant consists in placing the shaped catalysts in a flow tube and, at 20 to 100° C., passing over a halide, an acetate, an oxalate, a citrate or a nitrate of the above-described metals in dissolved form. Ion exchange of this type can be carried out, for example, on the hydrogen, ammonium or alkali metal form of the catalysts.

Another way of applying metals to the catalysts consists in impregnating the zeolitic material with, for example, a halide, acetate, oxalate, citrate, nitrate or oxide of the above-described metals in aqueous or alcoholic solution.

Both ion exchange and also impregnation can be followed by drying, or alternatively repeated calcination. In the case of metal-doped catalysts, an aftertreatment with hydrogen and/or with steam may be advantageous.

A further method of modifying the catalyst consists in subjecting the heterogeneous-catalytic material, in shaped or unshaped form, to treatment with acids, such as hydrochloric acid (HCl), hydrofluoric acid (HF), phosphoric acid ($H_3PO_4$), sulfuric acid ($H_2SO_4$), oxalic acid ($HO_2C-CO_2H$) or mixtures thereof.

A particular variant consists in treating the catalyst powder prior to its shaping with hydrofluoric acid (0.001 to 2 molar, preferably 0.05 to 0.5 molar) for 1 to 3 hours with reflux. The product is filtered off and washed and is then generally dried at 100 to 160° C. and calcined at 400 to 550° C.

A further particular embodiment consists in an HCl treatment of the heterogeneous catalysts following their shaping with binder. Here, the heterogeneous catalyst is usually treated for 1 to 3 hours at temperatures between 60 and 80° C. with a 3 to 25% strength, in particular with a 12 to 20% strength, hydrochloric acid, then washed, dried at 100 to 160° C. and calcined at 400 to 550° C.

Another possible modification of the catalyst is the exchange with ammonium salts, e.g. with $NH_4Cl$, or with mono-, di- or polyamines. For this, the heterogeneous catalyst shaped with binder is subjected to exchange with from 10 to 25% strength, preferably about 20% strength, $NH_4Cl$ solution, usually at 60 to 80° C., continuously for 2 h in heterogeneous catalyst/ammonium chloride solution in a weight ratio of 1:15, and then dried at 100 to 120° C.

A further modification which can be carried out on aluminum-containing catalysts is dealuminization, in which some of the aluminum atoms are replaced by silicon or the aluminum content of the catalysts is decreased by, for example, hydrothermal treatment. Hydrothermal dealuminization is advantageously followed by extraction with acids or complexing agents in order to remove non-lattice aluminum formed. The replacement of aluminum by silicon can be effected, for example, using $(NH_4)_2SiF_6$ or $SiCl_4$. Examples of dealuminizations of Y zeolites are given in Corma et al., Stud. Surf. Sci. Catal. 37 (1987), pages 495 to 503.

The catalysts can be used as strands having diameters of e.g. 1 to 4 mm, or as tablets having e.g. diameters of 3 to 5 mm for the hydroamination of the olefins.

The reaction of the olefin with ammonia and/or the primary amine in the presence of the inorganic solid-state acid can be carried out, for example, as described in EP-A-132 736, EP-A-752 409 and EP-A-822 179.

The procedure usually involves mixing ammonia and/or primary amine together with olefin in a molar ratio of from 1:1 to 10:1, preferably from 1:1 to 5:1, and carrying out the reaction in a fixed-bed reactor or in a fluidized bed at a pressure of from 40 to 700 bar, preferably 200 to 300 bar, and a temperature of from 80 to 400° C., preferably 250 to 350° C., in the gaseous phase or in the supercritical state. Alternatively, the reaction can be carried out in the liquid phase at a pressure of from 40 to 80 bar and a temperature of from 60 to 120° C. in a stirred-tank reactor, a solid-liquid moving bed or a flow tube.

One embodiment of this process involves mixing ammonia and/or the primary amine together with the olefin or the olefin mixture in the molar ratio of from 1:1 to 5:1, passing it to a fixed-bed reactor, which contains the inorganic solid-state acid, and carrying out the reaction at a pressure of from 100 to 300 bar, preferably 120 to 300 bar, in particular 140 to 290 bar, and a temperature of from 200 to 350° C., preferably 220 to 330° C., in particular 230 to 320° C., in the gaseous phase or in the supercritical state.

The position of the equilibrium and therefore the conversion to the desired hydroamination product is heavily dependent on the reaction pressure chosen. A high pressure favors the addition product, although for technical and cost reasons the pressure range up to 300 bar is generally the optimum. As well as being influenced by parameters such as ammonia/amine excess and catalyst, the selectivity of the reaction is influenced to a great extent by the temperature. Although the reaction rate of the addition reaction increases with increasing temperature, in some cases selectivity-reducing secondary reactions are also encouraged. In addition, a temperature increase is in most cases not advantageous from a thermodynamic viewpoint. The position of the temperature optimum with regard to conversion and selectivity is dependent on the constitution of the olefin, the primary amine used and the catalyst and is in most cases in the range from 200 to 350° C.

c)

In a further particular alternative, in the first process stage, an olefin, in particular an olefin of the formula I, is reacted with ammonia, a primary amine and/or a secondary amine, in particular ammonia, a primary amine and/or a secondary amine of the formula II, in the presence of a transition metal complex compound as catalyst or mixtures thereof under hydroamination conditions.

The reaction generally takes place according to the above reaction schemes 1 and 2 and the corresponding comments relating to these schemes.

Very particularly preferred olefins I are ethene ($R^1$, $R^2$, $R^3$ and $R^4$=H), propene ($R^1$, $R^2$ and $R^3$=H and $R^4$=$CH_3$) and 1,3-butadiene ($R^1$, $R^3$ and $R^4$=H and $R^2$=CH=$CH_2$).

In addition to ammonia, very particularly preferred amines are mono- and dialkylamines, such as monomethylamine, dimethylamine, monoethylamine, diethylamine, n-butylamine, isopropylamine, diisopropylamine and di-n-butylamine.

Hydroamination products starting from ethene and ammonia are mono-, di- and/or triethylamine, starting from ethene and monoethylamine: di- and/or triethylamine, starting from isobutene and ammonia: tert-butylamine, starting from 1,3-butadiene and ammonia: 1-amino-3-butene and/or 2-amino-3-butene, starting from 1,3-butadiene and n-butylamine: (2-butenyl)-n-butylamine and/or (3-butenyl)-n-butylamine, and starting from propylene and isopropylamine: diisopropylamine.

The transition metal complex compound used as catalyst is generally a complex compound of a metal of Group IIIB, IVB or VIII of the Periodic Table of the Elements.

Examples thereof are the compounds of rhodium or iridium described in U.S. Pat. No. 3,758,586, such as (cyclooctadiene)$_2$RhCl$_2$, RhCl$_3$, RhBr$_3$ and IrCl$_3$, for the addition of secondary aliphatic amines to ethylene to give aliphatic tertiary amines, the compounds of ruthenium and iron described in U.S. Pat. No. 4,454,321, such as $RuCl_3*xH_2O$, Ru(cyclopentadienyl)$_2$, [Ru(NH$_3$)$_4$(OH)Cl]Cl*2 H$_2$O, Fe(CO)$_5$, Fe$_2$(CO)$_9$, H$_2$Fe(CO)$_4$, Fe(butadiene) (CO)$_3$, Fe(CO)$_5$/tri-n-butylphospine, Fe(CO)$_5$/triphenylphosphite, for the addition of ammonia, primary amines or secondary amines to olefins, such as ethene, the compounds of platinum and palladium cited in the overview article by Th. E. Müuller and M. Beller in Chem. Rev. 1998, Vol. 98, No. 2, pages 675 to 703, on pages 679 to 680, such as PtX$_4^{2-}$(X=Cl$^-$, Br$^-$), for the hydroamination of olefins, the compounds of lanthanum, neodymium, samarium and lutetium cited in the abovementioned overview article by Th. E. Müller and M. Beller on pages 681 to 684, such as Cp*$_2$Ln-E (Cp*=pentamethylcyclopentadienyl or tetramethylcyclopentadienyl with bridge to the second tetramethylcyclopentadienyl ligand, Ln=La, Nd, Sm or Lu, E⊖H, CH(SiMe$_3$)$_2$ or N(SiMe$_3$)$_2$), for the hydroamination (in particular the intramolecular hydroamination) of olefins and the compounds of platinum, ruthenium, hafnium, zirconium, iridium and tantalum cited in the abovementioned overview article by Th. E. Müller and M. Beller on pages 684 to 686, such as Pt(PEt$_3$)$_2$(H)(NHPh), IrCl(C$_2$H$_4$)$_2$(PEt$_3$)$_2$ and Cp$_2$Zr(H)[N(t-Bu)(SiHMe$_2$)], for the hydroamination of olefins.

The reaction of the olefin with the ammonia and/or the amine can be carried out, for example, as described in the abovementioned literature.

The reaction can be carried out continuously, in a batch procedure or in a semibatch procedure.

In the case of the batch procedures, the catalyst is initially introduced together with the amine. After the reaction temperature has been reached, the olefin is injected. When the pressure has dropped (measure of the reaction), the product or product mixture is distilled off.

Excess olefin and amine which has not fully reacted can be recycled.

In the case of the batch procedure, the catalyst can be conveyed with the product mixture from the reactor via the still and worked up separately.

The reaction can be carried out in a stirred-tank reactor.

In the case of the continuous procedure, the reaction can be carried out in a bubble column. Here, the olefin is bubbled in from below through the mixture of catalyst and product solution. The solution can then be removed from the catalyst by distillation, or the catalyst can be removed from the product solution using a membrane. Alternatively, the catalyst does not need to be removed, but can be added directly to the work-up or to the next process step, provided it does not cause problems there.

Second Process Stage

The hydroamination product(s) resulting in the first process stage is/are then reacted in a second process stage under transalkylating conditions.

Preferably, the hydroamination product(s) resulting in the first process stage is/are then reacted in the second process stage d) in the presence of a transalkylating catalyst or e) in the presence of hydrogen and a transalkylating hydrogenation or dehydrogenation catalyst at temperatures of from 80 to 400° C.

The reaction discharge from the first process stage comprises hydroamination products, corresponding to the olefin/olefins and/or amine/amines used in each case and the hydroaminating conditions chosen in each case (see above). These hydroamination products generally have the formulae III, IV, V, VI, VII and/or VIII (see above reaction schemes 1 and 2 and the comments relating thereto).

The reaction discharge from the first process stage can, usually following removal of the catalyst (as described above in each case), be used directly in the second process stage.

However, it is also possible to firstly remove the hydroamination product(s) desired for the second process stage (as described above in each case) from the reaction discharge from the first process stage and then to use said product(s) in the second process stage.

Advantageously, ammonia and/or amines can also be passed to the feed for the second process stage, and/or ammonia and/or amines from the reaction discharge can be passed/recycled to this second process stage.

The reaction of the hydroamination product/products obtained in the first process stage in the second process stage under transalkylating conditions can be carried out, for example, as described in Houben Weyl volume XI/1, Nitrogen Compounds II, 1957, Georg Thieme Verlag Stuttgart, p. 248–261.

According to this, the amine transalkylation ('amine exchange') can be carried out in the presence of transalkylating catalysts, such as acids, metal salts, iodine, dehydration catalysts, hydrogenation/dehydrogenation catalysts, or else in the absence of catalysts.

Examples of acids which are suitable as transalkylating catalyst are hydrohalic acids (such as HCl), phosphoric acid, sulfanilic acid or sulfonic acids (such as p-toluenesulfonic acid).

Examples of metal salts which are suitable as transalkylating catalyst are zinc or iron halides, such as zinc chloride, iron(II) chloride or iron(III) chloride.

Examples of dehydration catalysts which are suitable as transalkylating catalyst are manganese(II) oxide/active carbon, aluminum silicates, Al$_2$O$_3$, TiO$_2$ or ZrO$_2$.

Preferred transalkylating catalysts are hydrogenation and dehydrogenation catalysts.

Here, the presence of hydrogen is advantageous to maintain the catalytic activity. Alternatively, the hydrogenation or dehydrogenation catalyst can be freed from deposits reductively using H$_2$ at regular intervals.

Particularly suitable hydrogenation and dehydrogenation catalysts are catalysts which comprise, as catalytically active constituents, elements chosen from the group copper, silver, gold, iron, cobalt, nickel, rhenium, ruthenium, rhodium, palladium, osmium, iridium, platinum, chromium, molybdenum and tungsten, in each case in metallic form (oxidation state 0) or in the form of compounds, such as oxides, which are reduced to the corresponding metal under the process conditions.

The catalytically active constituents copper, silver, gold, iron, cobalt, nickel, rhenium, ruthenium, rhodium, palladium, osmium, iridium, platinum, chromium, molybdenum and/or tungsten are generally present in total amounts of from 0.1 to 80% by weight, preferably 0.1 to 70% by weight, particularly preferably 0.1 to 60% by weight, calculated as metal in oxidation state 0, in the catalytically active mass of the catalyst.

Preference is given to catalysts which comprise, as catalytically active constituents, elements chosen from the group copper, silver, cobalt, nickel, ruthenium, rhodium, palladium, platinum, chromium and molybdenum, in particular chosen from the group copper, cobalt, nickel, in each case in metallic form (oxidation state 0) or in the form of compounds, such as oxides, which are reduced to give the corresponding metal under the process conditions.

More preferred catalysts are those which comprise the catalytically active constituents copper, silver, iron, cobalt, nickel, ruthenium, rhodium, palladium, osmium, iridium and/or platinum and a support material, preferably chosen from the group aluminum oxide, zirconium dioxide, titanium dioxide, carbon and/or oxygen-containing compounds of silicon.

The catalytically active mass of these catalysts preferably used in the process according to the invention generally comprises the catalytically active constituents copper, silver, iron, cobalt, nickel, ruthenium, rhodium, palladium, osmium, iridium and/or platinum in total amounts of from 0.1 to 80% by weight, preferably 0.1 to 70% by weight, particularly preferably 0.1 to 60% by weight, calculated as metal in oxidation state 0.

Furthermore, the catalytically active mass of these preferred catalysts generally comprises the support materials aluminum oxide ($Al_2O_3$), zirconium dioxide ($ZrO_2$), titanium dioxide ($TiO_2$), carbon and/or oxygen-containing compounds of silicon, calculated as $SiO_2$, in total amounts of from 20 to 99.9% by weight, preferably 30 to 99.9% by weight, particularly preferably 40 to 99.9% by weight.

Particular preference is given to catalysts having the active components Cu, Co, Ni and/or Pd, in particular Cu, Co and/or Ni. These can be used as uniform-composition catalysts or as supported catalysts.

Very particular preference is given to Cu-containing catalysts which, as has been recognized according to the invention, are more selective due to their comparatively low ethane or methane formation.

Examples thereof are copper alloys, metallic copper, e.g. in the form of copper gauze, and Cu catalysts with a Cu content of from 2 to 70% by weight of Cu, calculated as CuO, on a support, preferably with 10 to 55% by weight of Cu, calculated as CuO, on a support. Preferred support material may be aluminum oxide ($Al_2O_3$), zirconium dioxide ($ZrO_2$), titanium dioxide ($TiO_2$), carbon and/or oxygen-containing compounds of silicon.

For example, it is possible to use the catalysts disclosed in EP-A-382 049, the catalytically active mass of which prior to treatment with hydrogen comprises 20 to 85% by weight, preferably 70 to 80% by weight, of $ZrO_2$, 1 to 30% by weight, preferably 1 to 10% by weight, of CuO, and in each case 1 to 40% by weight, preferably 5 to 20% by weight, of CoO and NiO, for example the catalysts described in loc. cit. on page 6 having the composition 76% by weight of Zr, calculated as $ZrO_2$, 4% by weight of Cu, calculated as CuO, 10% by weight of Co, calculated as CoO, and 10% by weight of Ni, calculated as NiO, in the process according to the invention.

Furthermore, in the process according to the invention, it is possible to use the catalysts disclosed in EP-A-963 975, the catalytically active mass of which prior to treatment with hydrogen comprises 22 to 40% by weight of $ZrO_2$, 1 to 30% by weight of oxygen-containing compounds of copper, calculated as CuO, 15 to 50% by weight of oxygen-containing compounds of nickel, calculated as NiO, where the Ni:Cu molar ratio is greater than 15 to 50% by weight of oxygen-containing compounds of cobalt, calculated as CoO, 0 to 10% by weight of oxygen-containing compounds of aluminum and/or manganese, calculated as $Al_2O_3$ or $MnO_2$, and no oxygen-containing compounds of molybdenum, for example the catalyst A disclosed in loc. cit., page 17, having the composition 33% by weight of Zr, calculated as $ZrO_2$, 28% by weight of Ni, calculated as NiO, 11% by weight of Cu, calculated as CuO and 28% by weight of Co, calculated as CoO.

In the process according to the invention it is also possible to use catalysts disclosed in EP-A-514 692, the catalytically active mass of which prior to treatment with hydrogen comprises 5 to 100% by weight of an oxide of copper and nickel in the atomic ratio of from 1:1 to 10:1, preferably from 2:1 to 5:1, and zirconium and/or aluminum oxide, in particular the catalysts disclosed in loc. cit. on page 3, lines 20 to 30, the catalytically active mass of which prior to treatment with hydrogen comprises 20 to 80% by weight, particularly 40 to 70% by weight of $Al_2O_3$ and/or $ZrO_2$, 1 to 30% by weight of CuO, 1 to 30% by weight, of NiO and 1 to 30% by weight of CoO.

Preference is given according to the invention to using catalysts disclosed in DE-A-19 53 263 comprising cobalt, nickel and copper and aluminum oxide and/or silicon dioxide having a metal content of from 5 to 80% by weight, in particular 10 to 30% by weight, based on the overall catalyst, where the catalysts, calculated on the metal content, comprise 70 to 95% by weight of a mixture of cobalt and nickel and 5 to 30% by weight of copper, and where the weight ratio of cobalt to nickel is 4:1 to 1:4, in particular 2:1 to 1:2, the catalysts disclosed in EP-A-696 572, the catalytically active mass of which prior to reduction with hydrogen comprises 20 to 85% by weight of $ZrO_2$, 1 to 30% by weight of oxygen-containing compounds of copper, calculated as CuO, 30 to 70% by weight of oxygen-containing compounds of nickel, calculated as NiO, 0.1 to 5% by weight of oxygen-containing compounds of molybdenum, calculated as $MoO_3$, and 0 to 10% by weight of oxygen-containing compounds of aluminum and/or manganese, calculated as $Al_2O_3$ or $MnO_2$, for example the catalyst disclosed in loc. cit., page 8, having the composition 31.5% by weight of $ZrO_2$, 50% by weight of NiO, 17% by weight of CuO and 1.5% by weight of $MoO_3$, the catalysts, disclosed in EP-A-284 919, of the formula $M_xMg_y(SiO_2).nH_2O$, in which M is a divalent, reducible metal atom from the group Cu, Fe, Co and Ni, x and y are numbers which together can attain the value 1.5, and n after drying, expressed in % by weight, is between 0 and 80, for example the catalyst described in loc. cit. in the example, comprising 35% of CuO, 9% of MgO and 38% of $SiO_2$ and the catalyst described in EP-A-863 140 on page 3 comprising 45 to 47% by weight of CuO, magnesium silicate comprising about 15 to 17% by weight of MgO and 35 to 36% by weight of $SiO_2$, about 0.9% by weight of $Cr_2O_3$, about 1% by weight of BaO and about 0.6% by weight of ZnO, the catalysts disclosed in DE-A-24 45 303 obtainable by heat-treating a basic carbonate, containing copper and aluminum, of the general composition $Cu_mAl_6(CO_3)_{0.5m}O_3(OH)_{m+12}$, where m is any value between 2 and 6, including fractional values, at a temperature of from 350 to 700° C., for example the copper-containing precipitated catalyst disclosed in loc. cit, Example 1 and prepared by treating a solution of copper nitrate and aluminum nitrate with sodium bicarbonate and subsequently washing, drying and heat-treating the precipitate, and the supported catalysts disclosed in WO 95/32171 and EP-A-816 350, comprising 5 to 50% by weight, preferably 15 to 40% by weight, of copper, calculated as CuO, 50 to 95% by weight, preferably 60 to 85% by weight, of silicon, calculated as $SiO_2$, 0 to 20% by weight of magnesium, calculated as MgO, 0 to 5% by weight of barium, calculated as BaO, 0 to 5% by weight of zinc, calculated as ZnO, and 0 to 5% by weight of chromium, calculated as $Cr_2O_3$, in each case based on the total weight of the calcined catalyst, for example the catalyst disclosed in EP-A-816 350, page 5, comprising 30% by weight of CuO and 70% by weight of $SiO_2$.

The hydrogenation or dehydrogenation catalysts used in the process according to the invention as transalkylating catalyst can be prepared by processes described in the prior art and some are also available commercially.

In the preparation of supported catalysts no limitations of any kind exist with regard to the method of applying the active components, such as nickel, cobalt and/or copper and optionally further components, to the support material used.

In particular, the following methods of application are suitable:

a) Impregnation

Application of a metal salt solution in one or more impregnation stages to a prefabricated inorganic support. After the impregnation, the support is dried and, where appropriate, calcined.

a1) The impregnation can take place according to the so-called "incipient wetness" method, in which the support is wetted with the impregnation solution no further than saturation in accordance with its water absorption capacity. The impregnation can, however, also take place in supernatant solution.

a2) In the case of multistage impregnation methods, it is advantageous to dry and, where appropriate, to calcine between individual impregnation steps. Multistage impregnation is advantageously used when a relatively large amount of metal is to be applied to the support.

a3) The inorganic support material is preferably employed in the impregnation as preshaped mass, for example as powders, beads, strands or tablets. Particular preference is given to use as powders.

a4) The solvent preferably used for the metal salts is concentrated aqueous ammonia.

a5) Promoters can be incorporated in one step analogously to a1) by impregnation with a suitably metal-containing impregnation solution, e.g. copper-, cobalt- and/or nickel-containing impregnation solution, and promoter-containing impregnation solution, or in two or more stages analogously to a2) by alternate impregnation with metal-containing impregnation solution and promoter-containing impregnation solution.

b) Precipitation

Precipitation of a metal salt solution onto a prefabricated inert inorganic support. In a particularly preferred embodiment, the latter is in the form of a powder in an aqueous suspension.

b1) In one embodiment (i), a metal salt solution is precipitated, preferably with soda solution. The initial charge used is an aqueous suspension of the support material.

b2) In a further embodiment (ii), the precipitated catalyst can be produced in a two-stage process. This entails a powder being prepared and dried as indicated in a) in a first stage. This powder is converted into an aqueous suspension and used as initial charge in a manner equivalent to that described in variant (i).

b3) Promoters can be incorporated in one step analogously to b1) by precipitation of a metal-containing solution, or in two or more stages analogously to b2) by successive precipitation of a metal-containing solution and promoter-containing solution. In the last-mentioned case, the individual precipitations can follow directly one after the other or can be separated by a washing process and/or drying process and/or calcining process.

The starting substances for a) and/or b) which can be used are in principle all of the metal (I) and/or metal (II) salts which are soluble in the solvents used in the application, for example sulfates, nitrates, chlorides, carbonates, acetates, oxalates or ammonium complexes. Particular preference is given to using metal carbonate for processes in accordance with a), and metal nitrates for processes in accordance with b).

Precipitated deposits which result from a) or b) are filtered in the customary manner and preferably washed alkali-free.

It is also possible to incorporate a promoter component in suitable form into the filtered and, where appropriate, washed precipitate. Suitable forms are, for example, inorganic salts or complexes or organic compounds.

Both the end products from a) and also those from b) are dried at temperatures of from 50 to 150° C., preferably at 100 to 140° C. and, where appropriate, subsequently heat-treated, e.g. over a period of 2 hours, at relatively high temperature, i.e. generally 200 to 400° C., in particular at 200 to 220° C.

It is possible to incorporate a promoter component in suitable form either after the drying or after the heat-treatment. Suitable forms are, for example, inorganic salts or complexes or organic compounds. The incorporation is carried out here advantageously by intensive mixing, kneading and/or compaction, it also being possible, where appropriate, to add liquids, such as, for example, water or alcohols. Following incorporation of the promoter component, a further drying and/or heat-treatment step is advantageously carried out. In the case of addition in the dry state, however, this can also, where appropriate, be dispensed with.

For use in the process according to the invention, the above-described dried powder is preferably shaped to give tablets or similar moldings. The tableting auxiliary added for the shaping process is graphite, preferably in an amount of 3% by weight, based on the weight of the dried powder.

The tablet moldings are heat-treated at 300 to 600° C., in particular 330 to 350° C., preferably for 2 hours. This particular tableting method, compared to the exclusive use of graphite as tableting auxiliary in the customary methods, permits the powder to be shaped particularly readily to give tablets and produces very chemically and mechanically stable catalysts.

It is also possible to incorporate a promoter component in suitable form into the shaped tablets. Suitable forms are, for example, solutions of inorganic salts or complexes or organic compounds. Following incorporation, drying is advantageously carried out again at temperatures of from 50 to 150° C., preferably 100 to 140° C. In addition, heat-treatment can again be carried out, preferably for about 2 hours, at 300 to 600° C., in particular at 330 to 350° C.

If the reaction in the second process stage is carried out under transalkylating and also hydrogenating conditions, in particular in the presence of hydrogen and a transalkylating hydrogenation or dehydrogenation catalyst, unsaturated organic nitrogen compounds, i.e. organic nitrogen compounds which either have an olefinic C=C double bond (e.g. as in enamines and allylamines) or are imines, present in the hydroamination discharge from the first process stage can, where appropriate, be hydrogenated to give the correspondingly saturated amines.

The transalkylating hydrogenation or dehydrogenation catalysts are preferably the same hydrogenation and dehydrogenation catalysts as already described above.

The hydroamination discharge from the first process stage comprises e.g. unsaturated organic nitrogen compounds which have an olefinic C=C double bond if, in the first process stage, the olefin used was a di- or polyolefin or if, in the first process stage, the amine used was a correspondingly unsaturated amine. Imines can form as a result of double-bond isomerization or by β-elimination from metal alkylamides.

Examples of such di- or polyolefins are: 1,3-butadiene, 1,4-pentadiene, 1,5-hexadiene, allene, isoprene, 4-vinyl-1-cyclohexene, cyclohexadiene.

Examples of such unsaturated amines having an olefinic C=C double bond are: allylamine, 1-amino-2-butene, 1-amino-3-butene, 1-amino-4-pentene.

To carry out the second process stage, the preferred procedure involves passing the product or product mixture from the first reaction stage, or the amine or concentrated amine originating from the work-up of the first process stage continuously over a transalkylating catalyst, or carrying out the transalkylation discontinuously.

In a continuous procedure, the transalkylating catalyst is incorporated into a tubular reactor or tube-bundle reactor. In the case of a transalkylating dehydrogenation/hydrogenation reactor and the procedure in the presence of $H_2$ (variant e), the catalyst can, if desired, be reduced beforehand with hydrogen, although it can also be introduced directly in the presence of the product and hydrogen.

The hydrogen pressure chosen can be between 0 bar and 300 bar, preferably between 1 and 250 bar.

For a reaction in the gaseous phase, the pressure is generally 1 to 70 bar.

For a reaction in the liquid phase, the pressure is generally 70 to 250 bar.

The temperature is generally 80 to 400° C., in particular between 100 and 350° C., preferably between 120 and 250° C., very particularly preferably between 150 and 230° C.

Depending on the temperature chosen, a thermodynamic equilibrium of the alkylamines according to the process plus, possibly, ammonia is established which is dependent on the nitrogen to alkyl group ratio. The more sterically demanding the alkyl groups, the lower the proportion of the corresponding tertiary alkylamine.

The space velocity of starting material over the catalyst can be between 0.05 and 2 kg of starting material per liter of catalyst and per hour (kg/1*h), preferably between 0.1 and 1 kg/1*h, particularly preferably between 0.2 and 0.6 kg/1*h.

The molar ratio of the amines (the 'itransalkylating reagents') (in the preferred cases ammonia and/or primary amine) can vary within wide ranges depending on the desired product mix.

In the case of a discontinuous transalkylation, the catalyst can be initially introduced together with the starting material for the second process stage, and the desired amount of the transalkylating reagent can be added thereto or replenished. The mixture is then heated to the desired temperature (see above).

Following decompression, the discharge can be distilled.

A very particularly preferred embodiment of the process according to the invention is the reaction of ethene with monoethylamine and/or, preferably, diethylamine (first process stage) and subsequent reaction of the resulting ethylamines (in particular triethylamine) with ammonia (second process stage) and recycle of excess ammonia to the second process stage and partial recycle of monoethylamine and/or, preferably, diethylamine to the first process stage. The desired ethylamines as products of the process according to the invention are, where appropriate with recycle of excess ethylamines to the first and/or second process stage, obtained in any quantitative ratio to one another following work-up of the reaction discharge from the first and/or second process stage.

A further very particularly preferred embodiment of the process according to the invention is the reaction of propene with monoisopropylamine (first process stage) and subsequent reaction of the resulting diisopropylamine with ammonia (second process stage) and recycle of excess ammonia to the second process stage and partial recycle of monoisopropylamine to the first process stage. The desired isopropylamines as products of the process according to the invention are, where appropriate with recycle of excess isopropylamines to the first and/or second process stage, obtained in any quantitative ratio to one another following work-up of the reaction discharge from the first and/or second process stage.

Another very particularly preferred embodiment of the process according to the invention is the reaction of butadiene with n-monobutylamine and/or, preferably, n-dibutylamine (first process stage) and subsequent reaction of the resulting n-butylamines (in particular n-tributylamine) with ammonia (second process stage) and recycle of excess ammonia to the second process stage and partial recycle of n-monobutylamine and/or, preferably, n-dibutylamine to the first process stage. The desired n-butylamines are, where appropriate with recycle of excess n-butylamines to the first and/or second process stage, obtained in any quantitative ratio to one another following work-up of the reaction discharge from the first and/or second process stage.

The process according to the invention is described below in more detail using the preparation of ethylamines as an example. The description also applies analogously for the n-butylamines and isopropylamines and also for other alkylamines. The compositions of the streams given can be transferred accordingly with regard to their molar composition to the preparation of n-butylamines and isopropylamines.

These preferred processes are shown diagrammatically with the interconnection of the material streams on the block flow diagram FIG. 1 using the reaction of ethene with ammonia as an example.

Figure 1:
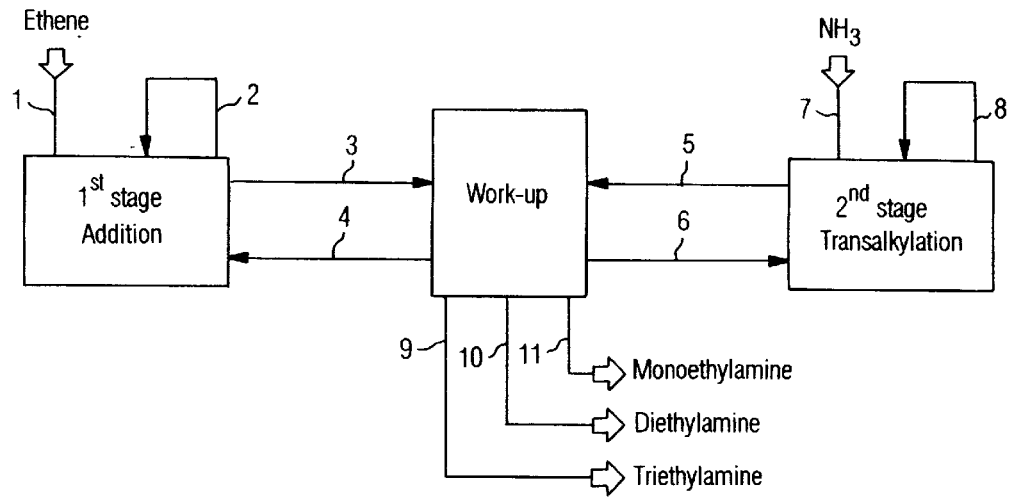
FIG. 1: Scheme for mono-, di- and triethylamine synthesis based on ethene and $NH_3$.
Figure 2:
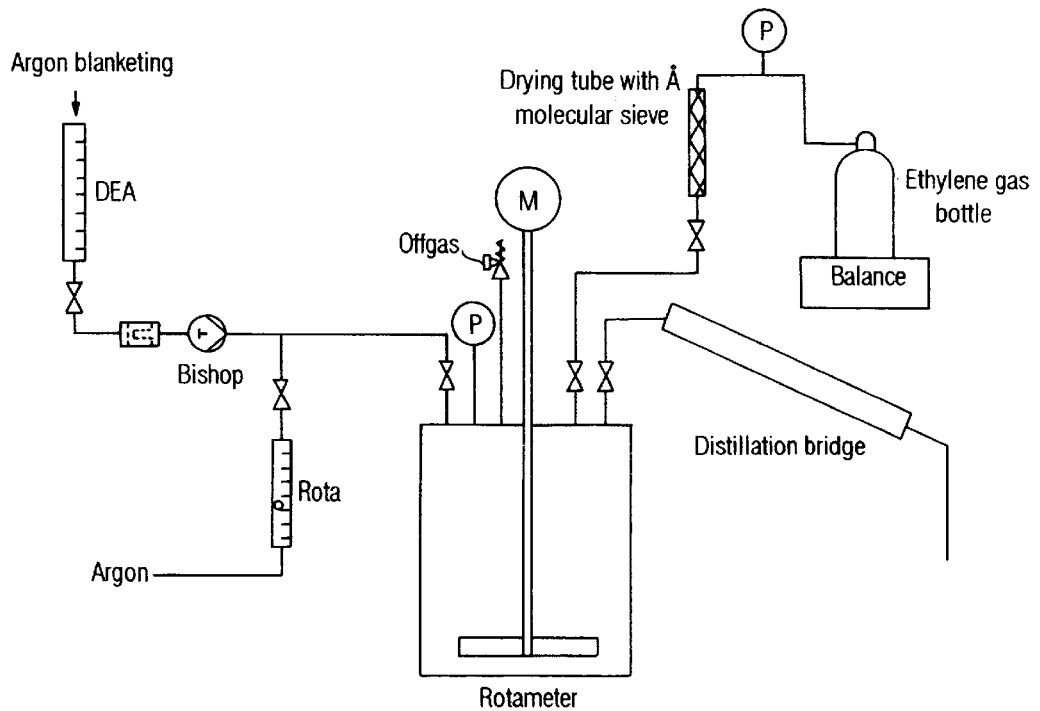
FIG. 2: Scheme for the reaction of diethylamine with ethylene in the presence of a sodium diethylamide catalyst.
Figure 3:
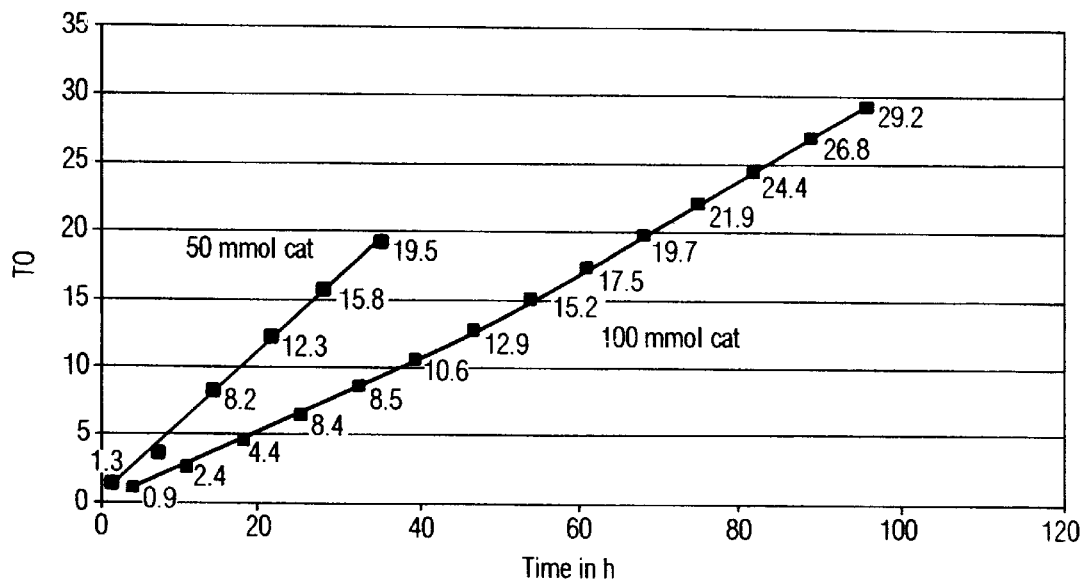
FIG. 3: Triethylamine formation by sodium diethylamide catalysis.

In the first process stage (e.g. according to Example 4) ethene is reacted with diethylamine and/or monoethylamine, preferably with diethylamine, in the presence of catalytic amounts of an alkali metal diethylamide (preparation of the alkali metal diethylamide e.g. according to Example 1) under hydroaminating conditions.

The streams (1; 2; 4) fed continuously to the reactor consist overall of 0–1% by weight, preferably <0.1% by weight, of ammonia, 0–5% by weight, preferably <1% by weight, of monoethylamine, 20–80% by weight, preferably 40–70% by weight, of diethylamine, 0–50% by weight, preferably <40% by weight, of triethylamine, 5–50% by weight, preferably 10–30% by weight, of ethylene, 0.01–10% by weight of the catalyst, preferably an alkali metal dialkylamide, and 0–20% by weight of a solvent for the catalyst. Suitable solvents are those already mentioned above in the rubric a).

In a discontinuous process, this stream data corresponds to the starting concentrations in the reactor.

The reaction can be carried out in various reactors, e.g. in a bubble column (preferably cascaded), a stirred-tank reactor, a jet loop reactor or a reactor cascade, usually at 40 to 150° C. and 1 to 100 bar, in particular at 70 to 120° C. and 3 to 20 bar.

The catalyst is homogeneously dissolved in the liquid phase. In principle, if the solubility of the catalyst is exceeded, the reactor can also be operated in the suspension procedure.

In the case of a discontinuous procedure set-up, the addition products (hydroamination products) formed are distilled off from the reactor. The catalyst, preferably an alkali metal dialkylamide, can remain in the reactor, provided it has sufficient activity, and can thus be used for further reactions.

In the case of the continuous procedure set-up, the adduct (triethylamine) formed can be removed form the reaction mixture, for example, by stripping with unreacted ethene. The reaction mixture can also be passed to a flash evaporation or a distillation, where the catalyst, which is dissolved or suspended in a high-boiling solvent (>50% by weight) or in trialkylamine (>50% by weight), is produced at the still. The catalyst-containing bottom product is returned to the reactor for the first process stage. A partial stream is removed to bleed out high-boiling components and catalyst. As an alternative to the thermal work-up of the reaction discharge, a filtration (nanofiltration, membrane filtration, etc.) can, for example, be used for catalyst recycle or retention.

The distillation discharge (stream 3) consisting of 30 to 100%, preferably 80–100%, of triethylamine is reacted in the second process stage (e.g. according to Example 7 or 8) with ammonia (ammonia feed: stream 7) in the presence of hydrogen over a transalkylating catalyst (e.g. the catalyst mentioned in Example 7 or Example 8) under heterogeneous catalysis at 1 to 250 bar and 100 to 300° C., in particular at 180 to 250° C. and 40 to 200 bar, to give a mixture of monoethylamine (5–70% by weight, preferably 10–30% by weight), diethylamine (20–80% by weight, preferably 30–60% by weight), triethylamine (5–70% by weight, preferably 15–50% by weight) and ammonia (1–70% by weight, preferably 2–10% by weight). The proportion of hydrogen is 0.1–50% by weight, preferably 0.5–5% by weight.

(The reactor exit stream arises overall from stream 5 and 8, and the reactor inlet stream consists of monoethylamine (0–50% by weight, preferably less than 30% by weight), diethylamine (0–60% by weight, preferably less than 30% by weight), triethylamine (10–95% by weight, preferably 30–80% by weight) and ammonia (1–70% by weight, preferably 3–50% by weight). The proportion of hydrogen is 0.1–50% by weight, preferably 0.5–5% by weight).

Suitable reactors are fluidized-bed reactors, moving-bed reactors and fixed-bed reactors, but preferably fixed-bed reactors. The reaction can be carried out in two phases, either as solid-liquid or solid-gaseous, and also in three phases.

The reaction discharge is then worked up using the customary processing methods in order to obtain the target products monoethylamine, diethylamine and triethylamine. Thus, the hot reaction discharge can be cooled e.g. by means of a quench or condenser, and the target products are condensed out. The gas phase which remains, consisting of ammonia, hydrogen and, according to their partial pressures, also the respective amines, is compressed to reaction pressure and returned to the reactor for the 2nd stage. The condensate or the liquid quench discharge (stream 5) are worked up in a suitable distillation sequence to give the products of value (stream 9; 10; 11) (see FIG. 1) in accordance with the desired specification. Ammonia or hydrogen dissolved in the condensate are removed and returned to the reactor together with the amounts of monoethylene and triethylamine required for the desired quantitative ratio of the three ethylamines (stream 6). If ammonia or hydrogen is produced in gaseous form, then these can be compressed or, preferably, absorbed with the distillate stream from the 1st stage. The distillate stream is then evaporated at reaction pressure and temperature and passed to the reactor for the 2nd stage.

The quantitative ratio of the three ethylamines to one another which is desired at the reactor exit of the $2^{nd}$ process stage can be adjusted within wide limits by varying the residence time and by the triethylamine/ammonia weight ratio, which is between 0.1–50 and, preferably, between 0.5–20, over the course of the second process stage. By recycling diethylamine to the $1^{st}$ and/or $2^{nd}$ stage, preferably of course to the $1^{st}$ stage for the reaction with ethylene to give triethylamine, and recycling monoethylamine and/or triethylamine to the $1^{st}$ and/or $2^{nd}$ stage, but preferably to the $2^{nd}$ stage, it is possible to prepare the amines in any quantitative ratio to one another. Including, the recycled amounts are the above-described composition of the reactor inlet stream ($1^{st}$ stage) produced.

The radicals $R^1$ to $R^7$ in the formula I to VIII are independently of one another:

$R^1$, $R^2$, $R^3$, $R^4$:

hydrogen (H), $C_1$- to $C_{20}$-alkyl, preferably $C_1$- to $C_{12}$-alkyl, particularly preferably $C_1$- to $C_8$-alkyl, such as methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl and isooctyl, $C_2$- to $C_{20}$-alkenyl, preferably $C_2$- to $C_{12}$-alkenyl, particularly preferably $C_2$- to $C_8$-alkenyl, such as vinyl and allyl, $C_3$- to $C_{20}$-cycloalkyl, preferably $C_3$- to $C_{12}$-cycloalkyl, particularly preferably $C_5$- to $C_8$-cycloalkyl, such as cyclopentyl, cyclohexyl, cycloheptyl and cyclooctyl, $C_5$- to $C_8$-cycloalkenyl, such as 2-cyclopent-1-yl, 2-cyclohex-1-yl, 3-cyclohex-1-yl, $C_6$- to $C_{20}$-alkylcycloalkyl, preferably $C_4$- to $C_{12}$-alkylcycloalkyl, particularly preferably $C_5$- to $C_{10}$-alkylcycloalkyl, such as 2-methylcyclopentyl and 4-methylcyclohexyl, $C_6$- to $C_{20}$-cycloalkylalkyl, preferably $C_4$- to $C_{12}$-cycloalkylalkyl, particularly preferably $C_5$- to $C_{10}$-cycloalkylalkyl, such as cyclopentylmethyl and cyclohexylmethyl, aryl, such as phenyl, 1-naphthyl and 2-naphthyl, preferably phenyl, $C_7$- to $C_{20}$-alkylaryl, preferably $C_7$- to $C_{16}$-alkylaryl, preferably $C_7$- to $C_{12}$-alkylphenyl, such as 2-methylphenyl, 3-methylphenyl, 4-methylphenyl, 2-ethylphenyl, 3-ethylphenyl and 4-ethylphenyl, $C_7$- to $C_{20}$-aralkyl, preferably $C_7$- to $C_{16}$-aralkyl, preferably $C_7$- to $C_{12}$-phenalkyl, such as phenylmethyl, 1-phenylethyl, 2-phenylethyl, $R^1$ and $R^3$:

together a $C_2$- to $C_{12}$-alkylene chain, preferably a $C_3$- to $C_8$-alkylene chain, particularly preferably —$(CH_2)_3$—, —$(CH_2)_4$—, —$(CH_2)_5$—, —$(CH_2)_6$— and —$(CH_2)_7$—, in particular —$(CH_2)_3$— and —$(CH_2)_4$—, $R^5$:

hydrogen (H), $R^5$, $R^6$:

$C_1$- to $C_{20}$-alkyl, $C_2$- to $C_{20}$-alkenyl, $C_3$- to $C_{20}$-cycloalkyl, in each case defined as above for $R^1$ to $R^4$, aralkyl, in particular $C_7$- to $C_{20}$-aralkyl, as defined above for $R^1$ to $R^4$, alkoxyalkyl, in particular $C_{2-30}$-alkoxyalkyl, preferably $C_{2-20}$-alkoxyalkyl, particularly preferably $C_{2-8}$-alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_2$- to $C_4$-alkoxyalkyl, aminoalkyl, in particular $C_{1-20}$-aminoalkyl, preferably $C_{1-8}$-aminoalkyl, such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl) aminomethyl, monoalkylaminoalkyl, in particular $C_{2-30}$-monoalkylaminoalkyl, preferably $C_{2-20}$-monoalkylaminoalkyl, particularly preferably $C_{2-8}$-monoalkylaminoalkyl, such as methylaminomethyl, 2-methylaminoethyl, ethylaminomethyl, 2-ethylaminoethyl and 2-isopropylaminoethyl, dialkylaminoalkyl, in particular $C_{3-30}$-dialkylaminoalkyl, preferably $C_{3-20}$-dialkylaminoalkyl, particularly preferably $C_{3-10}$-dialkylaminoalkyl, such as N,N-dimethylaminomethyl, (N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl and 2-(N,N-diisopropylamino)ethyl, $R^5$ and $R^6$:

together a saturated or unsaturated $C_3$- to $C_9$-alkylene chain which can be interrupted by an O, S or N heteroatom, such as —$(CH_2)_3$—, —$(CH_2)_4$—, —$(CH_2)_5$—, —$(CH_2)_6$—, —$(CH_2)_7$— and —CH=CH—CH=CH—, in particular together a —$(CH_2)_j$—X—$(CH_2)_k$— group, where j and k independently of one another =1, 2, 3 or 4 and X=$CH_2$, $CHR^7$, oxygen (O), sulfur (S) or $NR^7$, where $R^7$=H or $C_1$- to $C_4$-alkyl, such as methyl, ethyl, n-propyl, isopropyl, n-butyl, isobutyl, sec-butyl, tert-butyl, such as —$(CH_2)_2$—NH—$(CH_2)_2$—, —$(CH_2)_2$—$NCH_3$—$(CH_2)_2$—, —$(CH_2)_2$—O—$(CH_2)_2$—.

EXAMPLES

Example 1

Preparation of Sodium Diethylamide and Potassium Diethylamide $NaNEt_2$ and $KNEt_2$ were prepared in accordance with WO 93/14061 as follows: 100 mmol of Na or K were dispersed under argon in 30 ml of absolute, boiling toluene. The suspension was then cooled and, at 20° C., a mixture of 140 mmol of isoprene, 140 mmol of diethylamine and 35 ml of absolute toluene dried over a 3 Å molecular sieve was slowly added dropwise. During a post-stirring time of 1 h, $NaNEt_2$ or $KNEt_2$ finally formed. The product was centrifuged off from the solution under argon and transferred to a 100 ml steel autoclave using 19.1 g of $HNEt_2$ dried over a 3 Å molecular sieve.

Example 2

Preparation of Lithium Diethylamide

A 250 ml glass flask was charged, under argon, with 140 mmol of diethylamine dried over a 3 Å molecular sieve, and 100 mmol of BuLi (2.5M solution in hexane) were slowly added dropwise at 25° C., giving a suspension of $LiNEt_2$. The addition of a further 260 mmol of diethylamine resulted in a homogeneous solution which was transferred to a 100 ml steel autoclave.

Example 3

Preparation of Sodium Di-n-butylamide and Reaction of Di-n-butylamine with Butadiene in the Presence of Sodium Di-n-butylamide $NaNBu_2$ was prepared in accordance with WO 93/14061 as follows: 50 mmol of Na were dispersed in 30 ml of abs. n-octane under argon at 110° C. in a 250 ml glass flask. After cooling, a mixture consisting of 60 mmol of isoprene, 60 mmol of di-n-butylamine dried over a 3 Å molecular sieve and 30 ml of abs. n-octane was added dropwise, and the mixture was then stirred for 1 h. The sodium di-n-butylamide formed was centrifuged off under argon, dissolved in 640 mmol of di-n-butylamine and transferred to a 270 ml steel autoclave. This was heated to 80° C. and, with stirring, 475 mmol of butadiene were injected over the course of 5 h. After a post-stirring time of 1 h, the autoclave was cooled and opened, and the contents were treated with 25 mol of 10% by weight KCl in $H_2O$. The experiment was repeated twice more, and all organic phases were combined, dried with a 3 Å molecular sieve and hydroisomerized (see Example 9 below).

Example 4

Reaction of Diethylamine with Ethene in the Presence of Sodium Diethylamide as Catalyst 40 ml of diethylamine were pumped at room temperature into the autoclave from Example 1. After heating to 90° C., ethene was introduced in a slightly substoichiometric amount (7.2 g) and the mixture was stirred until the pressure dropped from initially 18 bar gage to 0 bar (7 h). The product mixture (diethylamine/triethylamine) was distilled out from the autoclave (boiling temperature: 105° C.). This procedure was repeated 15 times (29 turnover (TO)), without deactivation being apparent.

Example 5

Reaction of Diethylamine with Ethene in the Presence of Sodium Diethylamide as Catalyst The catalyst was prepared as in Example 1. Only 50 mmol of catalyst were used in the process. After heating to 90° C., ethene was introduced in a slightly substoichiometric amount (7.3 g) and the mixture was stirred until the pressure dropped from initially 19 bar gage to 2 bar gage (7 h). The product mixture (diethylamine/triethylamine) was distilled out from the autoclave (boiling temperature: 102° C.). This procedure was repeated 5 times (20 turnover (TO)), without deactivation being apparent.

It is notable here that despite a halved amount of catalyst the same amount of triethylamine was formed. Accordingly, only the dissolved sodium diethylamide is catalytically active.

Example 6

Reaction of Diethylamine with Ethene in the Presence of Butyllithium as Catalyst The autoclave from Example 2 was charged with 40 ml of diethylamine, and ethene (5.3 g) was injected. The mixture was heated, with stirring, to 90° C. (pressure: 21 bar) and stirred until a pressure drop was no longer observed (7 h) (pressure: 13.5 bar). After cooling to room temperature, 50 ml of product mixture were distilled out at atmospheric pressure and analyzed by GC: the solution comprised: 71% of DEA and 19% of TEA. This corresponds to 6 g of TEA.

Example 7

Reaction of Triethylamine with Ammonia (Isomerization)

A hydrogenation catalyst (10% by weight of CoO, 10% by weight of NiO and 4% by weight of CuO on $Al_2O_3$ in DE-A-19 53 263. Example 1) was incorporated into a continuously operated laboratory apparatus (60 ml tubular reactor) without recycle and started up without activation at a hydrogen pressure of 65 bar. Both the temperature and the ratio of ammonia to triethylamine were varied in the reactor feed. The space velocity of 0.2 kg/l*h (kg of triethylamine per liter of catalyst and per hour) was left constant:

a) Variation of the temperature:

a1)

At 65 bar (23 l of hydrogen (STP), the reactor was charged with 17 ml/h of ammonia and 16.55 ml/h of triethylamine (TEA). At 180° C. a discharge was obtained which consisted exclusively of monoethylamine (MEA) (25.3% by weight), diethylamine (DEA) (44.8% by weight) and TEA (29.9% by weight).

a2)

At 65 bar (23 l of hydrogen (STP)), the reactor was charged with 17 ml/h of ammonia and 16.55 ml/h of TEA. At 210° C., a discharge was obtained which consisted exclusively of MEA (32.5% by weight), DEA (52.3% by weight) and TEA (15.7% by weight).

b) Variation of the $NH_3$/TEA ratio in the reactor feed:

b1)

At 65 bar (23 l of hydrogen (STP)), the reactor was charged with 3.75 ml/h of ammonia and 12.4 ml/h of TEA. At 200° C. a discharge was obtained which consisted exclusively of MEA (12.6% by weight), DEA (49.9% by weight) and TEA (37.5% by weight).

b2)

At 65 bar (23 l of hydrogen (STP)), the reactor was charged with 15.1 ml/h of ammonia and 12.4 ml/h of TEA. At 200° C. a discharge was obtained which consisted exclusively of MEA (34.0% by weight), DEA (49.7% by weight) and TEA (20.3% by weight).

b3)

At 65 bar (23 l of hydrogen (STP)), the reactor was charged with 30.3 ml/h of ammonia and 12.4 ml/h of TEA. At 200° C. a discharge was obtained which consisted exclusively of MEA (47.2% by weight), DEA (44.7% by weight) and TEA (7.1% by weight).

Example 8

Reaction of Triethylamine with Ammonia (Isomerization) Over a Cu Catalyst

Figure 4:
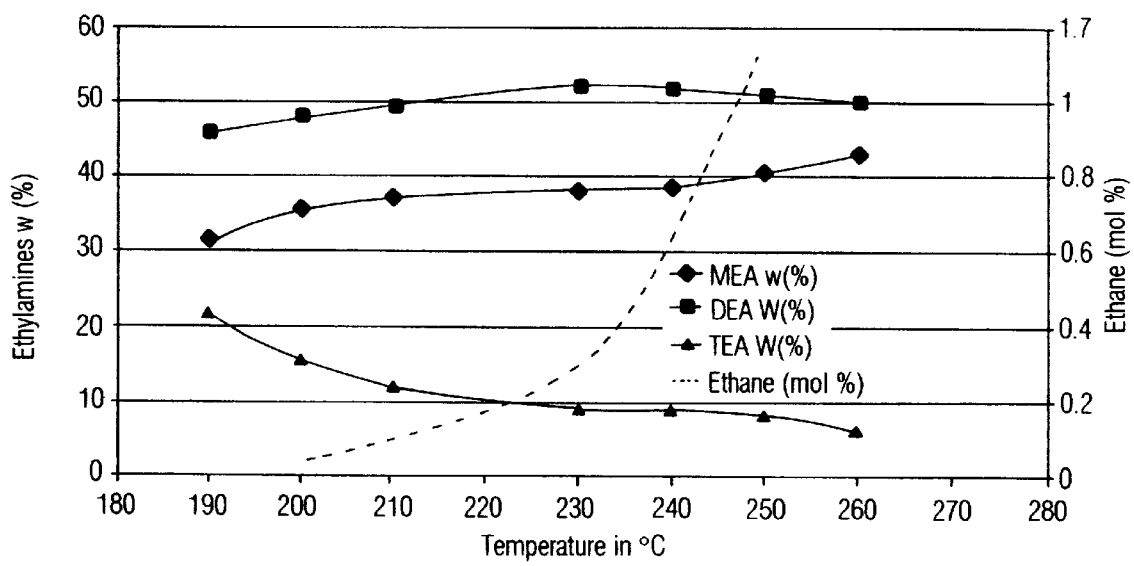
FIG. 4: Isomerization of triethylamine with ammonia at various temperatures (catalyst: 53% by weight of CuO on $Al_2O_3$).

An amination catalyst (53% by weight of CuO on $Al_2O_3$) in reduced and passivated form was incorporated into a continuously operated laboratory apparatus (60 ml tubular reactor) without recycle, and reduced for 6 h at 200° C. under a hydrogen atmosphere (atmospheric pressure). The apparatus was then started up at a hydrogen pressure of 65 bar. During the reaction both the temperature and the ratio of ammonia to triethylamine were varied. At a space velocity of 0.15 kg/l*h and a molar $NH_3$/TEA ratio of 4.3:1 the ethane formation was measured. Even at high temperatures of 250° C. the ethane formation remained in a range of less than 1 mol % (based on triethylamine) (see FIG. 4).

| Temp. | Ammonia | | TEA | | $NH_3$/TEA | Space velocity | $H_2$ | GC analysis | | |
|---|---|---|---|---|---|---|---|---|---|---|
| in ° C. | mol/h | g/h | mol/h | ml/h | mol/mol | kg/l*h | l/h (STP) | MEA | DEA | TEA |
| 190 | 0.142 | 2.42 | 0.0889 | | 1.6 | 0.15 | | 19.0 | 48.5 | 32.5 |
| 200 | 0.142 | 2.42 | 0.0889 | | 1.6 | 0.15 | | 19.8 | 51.1 | 29.1 |
| 210 | 0.142 | 2.42 | 0.0889 | | 1.6 | 0.15 | | 22.6 | 53.2 | 24.2 |
| 230 | 0.142 | 2.42 | 0.0889 | | 1.6 | 0.15 | | 23.3 | 56.7 | 20.0 |
| 190 | 0.234 | 4 | 0.0889 | | 2.6 | 0.15 | | 23.6 | 47.1 | 29.3 |
| 200 | 0.234 | 4 | 0.0889 | | 2.6 | 0.15 | | 27.3 | 50.5 | 21.9 |
| 210 | 0.234 | 4 | 0.0889 | | 2.6 | 0.15 | | 28.7 | 52.6 | 18.7 |
| 230 | 0.234 | 4 | 0.0889 | | 2.6 | 0.15 | | 32.9 | 54.6 | 12.3 |
| 190 | 0.38 | 6.5 | 0.0889 | | 4.3 | 0.15 | | 31.3 | 46 | 21.9 |
| 200 | 0.38 | 6.5 | 0.0889 | | 4.3 | 0.15 | | 35.6 | 48.2 | 15.7 |
| 210 | 0.38 | 6.5 | 0.0889 | | 4.3 | 0.15 | | 37.3 | 49.9 | 12.3 |
| 230 | 0.38 | 6.5 | 0.0889 | | 4.3 | 0.15 | | 38.1 | 52.3 | 9.2 |
| 240 | 0.38 | 6.5 | 0.0889 | | 4.3 | 0.15 | | 38.6 | 51.9 | 9.1 |
| 250 | 0.38 | 6.5 | 0.0889 | | 4.3 | 0.15 | | 40.3 | 51 | 8.4 |
| 260 | 0.38 | 6.5 | 0.0889 | | 4.3 | 0.15 | | 42.9 | 50.1 | 6.5 |

Explanatory remarks for the results table above:
The space velocity of the catalyst was left constant during the reaction at 0.15 kg of triethylamine per liter of catalyst and per hour (kg/l*h).
The amount of hydrogen was 23 liters (STP) per hour.
GC analysis: data for the components MEA (monoethylamine), DEA (diethylamine) and TEA (triethylamine) in GC area % (GC column: capillary column 30 m long, 1.5 μm, 0.32 mm Rtx-5-amines, temperature program: 50° C. (5 min.), then heating at 15° C./min.).

Example 9

Isomerization of Dibutylbutenylamine Mixture from the Reaction of Dibutylamine and Butadiene In a continuously operated tubular reactor (length 30 cm, volume 130 cm³, cat. volume: 50 ml), at a hydrogen pressure of 10 bar (10 l (STP)) and a space velocity of 0.3 kg/l*h for the reaction discharge from a reaction of butadiene with di-n-butylamine (Example 3), the proportion of ammonia was varied between 0.65 and 2.69 molar ratios. At a temperature of 230° C., the Cu catalyst described in Example 8 was used. The reaction discharge was analyzed using gas chromatography (as in Example 8). The ratios of the three amines monobutylamine (MBA), dibutylamine (DBA) and tributylamine (TBA) increase at the expense of the MBAs as the amount of ammonia increases (see table).

The present mixture was passed as in Experiment 9 with ammonia ($NH_3$ to di-n-butylbut-2-(E/Z)enyl/di-n-butylbut-1-(E/Z)enyl/di-n-butylbut-3-enyl mixture=1.67 to 1) with a space velocity of 0.3 kg/l*h and 230° C./10 bar/10 l of $H_2$ (STP) over the Cu catalyst described in Example 8. This gave a reaction mixture comprising 14.3% by weight of mono-n-butylamine (MBA), 53.9% by weight of di-n-butylamine (DBA) and 30.4% by weight of tri-n-butylamine (TBA).

| Temp. in °C. | Pressure in bar | $H_2$ l/h (STP) | Starting material g/h | Starting material mmol/h | $NH_3$ g/h | $NH_3$ mmol/h | $NH_3$/ DBBA | MBA in % | DBA in % | TBA in % |
|---|---|---|---|---|---|---|---|---|---|---|
| 230 | 10 | 10 | 15 | 81 | — | — | — | 0.56 | 18.34 | 66.05 |
| 230 | 10 | 10 | 15 | 81 | 0.9 | 53 | 0.65 | 8.19 | 44.17 | 33.54 |
| 230 | 10 | 10 | 15 | 81 | 2.6 | 153 | 1.89 | 17.97 | 48.93 | 19.31 |
| 230 | 10 | 10 | 15 | 81 | 3.7 | 218 | 2.69 | 22.03 | 48.71 | 15 |

(DBBA = dibutylbutylenamine)

Example 10

Preparation of Dibutylbutenylamine ("One-pot") and Subsequent Isomerization 50 mmol of Na were melted in 30 ml of anhydrous n-octane at 110° C. and dispersed by stirring. After cooling, 476.4 g of di-n-butylamine dried over a 3 Å molecular sieve were added, and 4 l/h of butadiene were passed over at atmospheric pressure with stirring. After 1.5 h, the temperature was increased to 60° C., and butadiene was passed over for a further 8 h. The reaction was then stopped by adding 30 ml of aqueous 30% strength by weight NaOH, and the organic phase was evaporated off, dried with a 3 Å molecular sieve and analyzed using GC.

| Substance | GC area % |
|---|---|
| Butadiene | 0.155 |
| 2-Butenes | 0.064 |
| Di-n-butylamine | 21.818 |
| 4-Vinylcyclohexene | 0.118 |
| Di-n-Butylbutenyl-amines | 77.823 |

Preliminary remarks relating to Examples 11 to 14

The basis of the examples listed below are, for the $1^{st}$ and $2^{nd}$ process stage, discontinuous autoclave experiments (Examples 4, 5 and 6 with regard to the $1^{st}$ process stage) and continuous transalkylating experiments (Examples 7 and 8 with regard to the $2^{nd}$ process stage).

Figure 5:
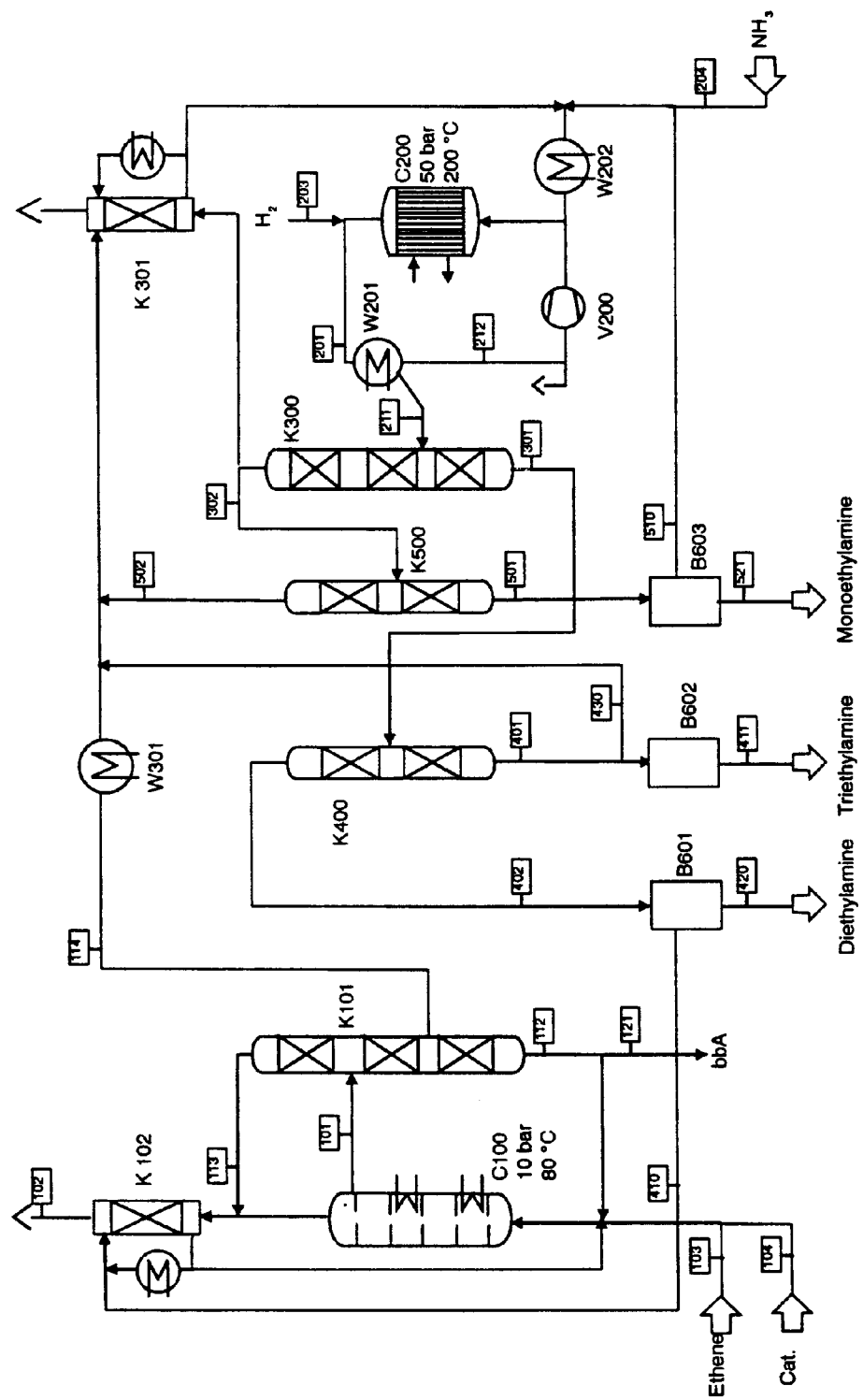
FIG. 5: Process scheme used for the simulation of the workup of the reaction discharges using thermodynamic data.

The work-up of the reaction discharges was simulated using thermodynamic data. The thermodynamic data of the pure substances originates from the DIPPR databank [Design Institute of Physical Properties Data, Version 11.0]. The binary systems were described using an NRTL Aspen approach. The approach was based both on our own series of measurements and also on UNIFAC estimations (increment method). The energy and material balances were calculated using an equation solver. The stream numbers given refer to the block diagram FIG. 1. The process scheme on which the simulation is based is shown in FIG. 5. The process scheme is applicable to Examples 11–14. The stream amounts and stream compositions, however, apply only to Example 11.

| Stream | | 1 | 2 | 3 | 4 | 5 | 6 | 7 | 8 | 9 | 10 | 11 |
|---|---|---|---|---|---|---|---|---|---|---|---|---|
| Amount | [kg/h] | 137.5 | 58.6 | 515.6 | 378.3 | 875.1 | 825 | 50.2 | 66.0 | 80.0 | 27.5 | 80.0 |
| Monoethyl amine | [kg/h] | 0.0 | 0.0 | 0.1 | 0.1 | 125.7 | 45.8 | 0.0 | 10.0 | 0.0 | 0.0 | 79.9 |
| Diethylamine | [kg/h] | 0.0 | 20.4 | 19.4 | 377.8 | 405.6 | 19.7 | 0.0 | 8.1 | 0.1 | 27.5 | 0.0 |
| Triethylamine | [kg/h] | 0.0 | 24.4 | 496.1 | 0.4 | 310.1 | 725.9 | 0.0 | 2.0 | 79.9 | 0.0 | 0.0 |
| Ammonia | [kg/h] | 0.0 | 0.0 | 0.0 | 0.0 | 33.6 | 33.6 | 50.2 | 16.4 | 0.0 | 0.0 | 0.1 |
| Ethene | [kg/h] | 137.5 | 8.0 | 0.0 | 0.0 | 0.0 | 0.0 | 0.0 | 0.0 | 0.0 | 0.0 | 0.0 |
| Cat. ($1^{st}$ stage) | [kg/h] | 0.0 | 5.7 | 0.0 | 0.0 | 0.0 | 0.0 | 0.0 | 0.0 | 0.0 | 0.0 | 0.0 |
| $H_2$ | [kg/h] | 0.0 | 0.0 | 0.0 | 0.0 | 0.0 | 0.0 | 0.0 | 29.6 | 0.0 | 0.0 | 0.0 |

| Stream |  | 1 | 2 | 3 | 4 | 5 | 6 | 7 | 8 | 9 | 10 | 11 |
|---|---|---|---|---|---|---|---|---|---|---|---|---|
| Amount | [kg/h] | 116.7 | 49.7 | 437.6 | 321.0 | 882.3 | 811 | 71.0 | 126.4 | 0.0 | 0.0 | 187.5 |
| Monoethylamine | [kg/h] | 0.0 | 0.0 | 0.0 | 0.1 | 212.1 | 24.8 | 0.0 | 14.6 | 0.0 | 0.0 | 187.3 |
| Diethylamine | [kg/h] | 0.0 | 17.3 | 16.5 | 320.6 | 320.9 | 16.7 | 0.0 | 5.5 | 0.0 | 0.0 | 0.0 |
| Triethylamine | [kg/h] | 0.0 | 20.7 | 421.0 | 0.3 | 180.2 | 600.9 | 0.0 | 1.0 | 0.0 | 0.0 | 0.0 |
| Ammonia | [kg/h] | 0.0 | 0.0 | 0.0 | 0.0 | 169.1 | 168.9 | 71.0 | 71.2 | 0.0 | 0.0 | 0.2 |
| Ethene | [kg/h] | 116.7 | 6.8 | 0.0 | 0.0 | 0.0 | 0.0 | 0.0 | 0.0 | 0.0 | 0.0 | 0.0 |
| Cat. (1$^{st}$ stage) | [kg/h] | 0.0 | 4.9 | 0.0 | 0.0 | 0.0 | 0.0 | 0.0 | 0.0 | 0.0 | 0.0 | 0.0 |
| H$_2$ | [kg/h] | 0.0 | 0.0 | 0.0 | 0.0 | 0.0 | 0.0 | 0.0 | 34.1 | 0.0 | 0.0 | 0.0 |

| Stream |  | 1 | 2 | 3 | 4 | 5 | 6 | 7 | 8 | 9 | 10 | 11 |
|---|---|---|---|---|---|---|---|---|---|---|---|---|
| Amount | [kg/h] | 144.0 | 61.3 | 540.0 | 396.1 | 1258.7 | 1215 | 43.7 | 94.9 | 0.0 | 187.5 | 0.0 |
| Monoethylamine | [kg/h] | 0.0 | 0.0 | 0.1 | 0.1 | 180.8 | 180.8 | 0.0 | 14.4 | 0.0 | 0.0 | 0.0 |
| Diethylamine | [kg/h] | 0.0 | 21.3 | 20.4 | 395.7 | 583.4 | 20.8 | 0.0 | 11.6 | 0.0 | 187.3 | 0.0 |
| Triethylamine | [kg/h] | 0.0 | 25.6 | 519.5 | 0.4 | 446.1 | 965.0 | 0.0 | 2.8 | 0.0 | 0.2 | 0.0 |
| Ammonia | [kg/h] | 0.0 | 0.0 | 0.0 | 0.0 | 48.4 | 48.4 | 43.7 | 23.6 | 0.0 | 0.0 | 0.0 |
| Ethene | [kg/h] | 144.0 | 8.4 | 0.0 | 0.0 | 0.0 | 0.0 | 0.0 | 0.0 | 0.0 | 0.0 | 0.0 |
| Cat. (1$^{st}$ stage) | [kg/h] | 0.0 | 6.0 | 0.0 | 0.0 | 0.0 | 0.0 | 0.0 | 0.0 | 0.0 | 0.0 | 0.0 |
| H$_2$ | [kg/h] | 0.0 | 0.0 | 0.0 | 0.0 | 0.0 | 0.0 | 0.0 | 42.5 | 0.0 | 0.0 | 0.0 |

| Stream |  | 1 | 2 | 3 | 4 | 5 | 6 | 7 | 8 | 9 | 10 | 11 |
|---|---|---|---|---|---|---|---|---|---|---|---|---|
| Amount | [kg/h] | 156.1 | 66.5 | 585.3 | 429.4 | 882.9 | 851 | 31.6 | 49.2 | 187.5 | 0.0 | 0.0 |
| MEA | [kg/h] | 0.0 | 0.1 | 0.1 | 0.1 | 88.8 | 88.8 | 0.0 | 6.5 | 0.0 | 0.0 | 0.0 |
| DEA | [kg/h] | 0.0 | 23.1 | 22.1 | 428.9 | 429.3 | 22.2 | 0.0 | 7.9 | 0.2 | 0.0 | 0.0 |
| TEA | [kg/h] | 0.0 | 27.7 | 563.2 | 0.4 | 349.8 | 725.3 | 0.0 | 2.1 | 187.3 | 0.0 | 0.0 |
| NH$_3$ | [kg/h] | 0.0 | 0.0 | 0.0 | 0.0 | 15.1 | 15.1 | 31.6 | 6.8 | 0.0 | 0.0 | 0.0 |
| Ethene | [kg/h] | 156.1 | 9.1 | 0.0 | 0.0 | 0.0 | 0.0 | 0.0 | 0.0 | 0.0 | 0.0 | 0.0 |
| Cat. | [kg/h] | 0.0 | 6.5 | 0.0 | 0.0 | 0.0 | 0.0 | 0.0 | 0.0 | 0.0 | 0.0 | 0.0 |
| H$_2$ | [kg/h] | 0.0 | 0.0 | 0.0 | 0.0 | 0.0 | 0.0 | 0.0 | 25.9 | 0.0 | 0.0 | 0.0 |

Regarding the above figure (Appendix 1):

This shows a simulated process variant taking the essential materials into account. The synthesis is simplified. The composition of the streams refers to Example 11. The stream numbers (1–11) according to the block diagram FIG. 1 correspond as follows to the above stream numbers:

1=103, 2=112+113, 3=114, 4=410, 5=211, 6=502+430+114, 7=204, 8=212, 9=411, 10=420, 11=521.

The 1$_{st}$ process stage consists of the reactor C100, the column K101 (head pressure: 5 bar, head temperature: 88° C., still temperature: 154° C., theoretical plates: 10) and the absorber K102. The second process stage consists of the reactor C200, the condenser W201, the evaporator W202, the compressor V200 and the absorber K301. The work-up consists of the sequence of distillation columns K300 (head pressure: 5 bar, head temperature: 50° C., still temperature: 123° C., theoretical number of plates: 18), K400 (head pressure: 2 bar, head temperature: 77° C., still temperature: 114° C., theoretical number of plates: 15) and K500 (head pressure: 5 bar, head temperature: 36° C., still temperature: 64° C., theoretical number of plates: 6).

| Stream |  | 101 | 102 | 103 | 104 | 112 | 113 | 114 | 121 | 201 | 203 | 204 | 211 | 212 |
|---|---|---|---|---|---|---|---|---|---|---|---|---|---|---|
| Amount | [kg/h] | 574.2 | 0.1 | 137.5 | 0.0 | 28.7 | 29.8 | 515.6 | 0.1 | 941.2 | 0.0 | 50.2 | 875.1 | 66.0 |
| Monoethylamine | [% by weight] | 0.0 | 0.0 | 0.0 | 0.0 | 0.0 | 0.1 | 0.0 | 0.0 | 14.4 | 0.0 | 0.0 | 14.4 | 15.1 |
| Diethylamine | [% by weight] | 6.9 | 4.5 | 0.0 | 0.0 | 0.2 | 68.1 | 3.8 | 0.2 | 44.0 | 0.0 | 0.0 | 46.4 | 12.3 |
| Triethylamine | [% by weight] | 90.7 | 19.8 | 0.0 | 0.0 | 79.8 | 5.0 | 96.2 | 79.8 | 33.2 | 0.0 | 0.0 | 35.4 | 3.0 |
| Ammonia | [% by weight] | 0.0 | 0.0 | 0.0 | 0.0 | 0.0 | 0.0 | 0.0 | 0.0 | 5.3 | 0.0 | 100.0 | 3.8 | 24.8 |
| Ethene | [% by weight] | 1.4 | 75.7 | 100.0 | 0.0 | 0.0 | 26.8 | 0.0 | 0.0 | 0.0 | 0.0 | 0.0 | 0.0 | 0.0 |
| Cat. (1$^{st}$ stage) | [% by weight] | 1.0 | 0.0 | 0.0 | 100.0 | 20.0 | 0.0 | 0.0 | 20.0 | 0.0 | 0.0 | 0.0 | 0.0 | 0.0 |
| H$_2$ | [% by weight] | 0.0 | 0.0 | 0.0 | 0.0 | 0.0 | 0.0 | 0.0 | 0.0 | 3.1 | 100.0 | 0.0 | 0.0 | 44.8 |

| Stream | | 301 | 302 | 401 | 402 | 410 | 411 | 420 | 430 | 501 | 502 | 510 | 521 |
|---|---|---|---|---|---|---|---|---|---|---|---|---|---|
| Amount | [kg/h] | 715.8 | 159.3 | 310.0 | 405.8 | 378.3 | 80.0 | 27.5 | 230.0 | 84.6 | 74.7 | 4.6 | 80.0 |
| Monoethylamine | [% by weight] | 0.0 | 78.9 | 0.0 | 0.0 | 0.0 | 0.0 | 0.0 | 0.0 | 99.9 | 55.1 | 99.9 | 99.9 |
| Diethylamine | [% by weight] | 56.7 | 0.0 | 0.1 | 99.9 | 99.9 | 0.1 | 99.9 | 0.1 | 0.0 | 0.0 | 0.0 | 0.0 |
| Triethylamine | [% by weight] | 43.3 | 0.0 | 99.9 | 0.1 | 0.1 | 99.9 | 0.1 | 99.9 | 0.0 | 0.0 | 0.0 | 0.0 |
| Ammonia | [% by weight] | 0.0 | 21.1 | 0.0 | 0.0 | 0.0 | 0.0 | 0.0 | 0.0 | 0.1 | 44.9 | 0.1 | 0.1 |
| Ethene | [% by weight] | 0.0 | 0.0 | 0.0 | 0.0 | 0.0 | 0.0 | 0.0 | 0.0 | 0.0 | 0.0 | 0.0 | 0.0 |
| Cat. (1st stage) | [% by weight] | 0.0 | 0.0 | 0.0 | 0.0 | 0.0 | 0.0 | 0.0 | 0.0 | 0.0 | 0.0 | 0.0 | 0.0 |
| $H_2$ | [% by weight] | 0.0 | 0.0 | 0.0 | 0.0 | 0.0 | 0.0 | 0.0 | 0.0 | 0.0 | 0.0 | 0.0 | 0.0 |

We claim:

1. A process for the preparation of alkylamines, which comprises, in a first process stage, reacting an olefin with ammonia, a primary amine and/or a secondary amine under hydroaminating conditions, and then, in a second process stage, reacting the resulting hydroamination product(s) under transalkylating conditions.

2. A process as claimed in claim 1, wherein, in the balance of the feed materials olefin and ammonia, primary amine and/or secondary amine, only ammonia and olefin are consumed.

3. A process as claimed in claim 1, wherein the reaction in the second process stage is carried out under transalkylating and hydrogenating conditions.

4. A process as claimed in claim 1, wherein, in the first process stage, an olefin is reacted
   a) with a primary amine and/or a secondary amine in the presence of a metal monoalkylamide or metal dialkylamide as catalyst or
   b) with ammonia and/or a primary amine in the presence of an inorganic solid-state acid as catalyst or
   c) with ammonia, a primary amine and/or a secondary amine in the presence of a transition metal complex compound as catalyst, and then, in the second process stage, the resulting hydroamination product(s) is/are reacted
   d) in the presence of a transalkylating catalyst or
   e) in the presence of hydrogen and a transalkylating hydrogenation or dehydrogenation catalyst at temperatures of from 80 to 400° C.

5. A process as claimed in claim 1, wherein the reaction in the second process stage is carried out in the presence of ammonia.

6. A process as claimed in claim 1, wherein the product mixture obtained in the second process stage is separated into product(s) which is/are returned to the first process stage, and/or product(s) which is/are returned to the second process stage, and the desired alkylamine(s).

7. A process as claimed in claim 1, wherein the reaction in the second process stage is carried out in the presence of hydrogen and a transalkylating hydrogenation or dehydrogenation catalyst, where, in the same process step, unsaturated alkylamines and/or corresponding imines are hydrogenated to give the corresponding alkylamines.

8. A process as claimed in claim 1, wherein the reaction in the second process stage is carried out continuously in the presence of a hydrogenation or dehydrogenation catalyst in a fixed bed.

9. A process as claimed in claim 1, wherein the reaction in the second process stage is carried out in the presence of a copper-containing catalyst, which may contain a support material, and hydrogen.

10. A process as claimed in claim 1, wherein the reaction in the first process stage is carried out in the presence of an alkali metal dialkylamide or zeolite as catalyst.

11. A process as claimed in claim 1, wherein the reaction in the first process stage is carried out in the presence of a sodium dialkylamide as catalyst.

12. A process as claimed in claim 1, wherein, in the first process stage, an olefin is reacted with a primary amine and/or a secondary amine in the presence of a metal monoalkylamide or metal dialkylamide or a transition metal complex compound as catalyst, and then, in the second process stage, the resulting hydroamination product(s) is/are reacted in the presence of ammonia and with conversion of the ammonia in the second process stage under transalkylating conditions, and then the product mixture obtained in the second process stage is separated into product(s) which is/are returned to the first process stage, and/or product(s) which is/are returned to the second process stage, and desired alkylamine(s).

13. A process as claimed in claim 1, wherein, in the first process stage, an olefin is reacted with ammonia, a primary amine and/or a secondary amine under hydroaminating conditions, and then, in the second process stage, the resulting hydroamination product(s) is/are reacted in the presence of ammonia and/or the primary amine under transalkylating conditions.

14. A process as claimed in claim 1, wherein the olefin is ethene, the primary amine is monoethylamine, the secondary amine is diethylamine and the alkylamines prepared in accordance with the process are monoethylamine, diethylamine and triethylamine.

15. A process as claimed in claim 1, wherein the olefin is 1,3-butadiene, the primary amine is mono-n-butylamine, the secondary amine is di-n-butylamine and the alkylamines prepared in accordance with the process are mono-n-butylamine, di-n-butylamine and tri-n-butylamine.

16. A process as claimed in claim 1, wherein the olefin is propene, the primary amine is monoisopropylamine and the alkylamines prepared in accordance with the process are monoisopropylamine and diisopropylamine.

* * * * *